(12) United States Patent
Schmidt et al.

(10) Patent No.: US 7,444,053 B2
(45) Date of Patent: Oct. 28, 2008

(54) INTEGRATED ELECTRICAL AND OPTICAL SENSOR FOR BIOMOLECULE ANALYSIS WITH SINGLE MOLECULE SENSITIVITY

(75) Inventors: Holger Schmidt, Capitola, CA (US); Aaron Roe Hawkins, Provo, UT (US); David W. Deamer, Santa Cruz, CA (US)

(73) Assignees: The Regents of the University of California, Oakland, CA (US); Brigham Young University, Provo, UT (US)

( * ) Notice: Subject to any disclaimer, the term of this patent is extended or adjusted under 35 U.S.C. 154(b) by 206 days.

(21) Appl. No.: 11/376,442

(22) Filed: Mar. 14, 2006

(65) Prior Publication Data

US 2006/0251371 A1     Nov. 9, 2006

Related U.S. Application Data

(63) Continuation-in-part of application No. 11/251,014, filed on Oct. 14, 2005, now Pat. No. 7,248,771, and a continuation-in-part of application No. 10/868,475, filed on Jun. 15, 2004, now Pat. No. 7,149,396.

(60) Provisional application No. 60/479,376, filed on Jun. 16, 2003.

(51) Int. Cl.
    *G02B 6/10*     (2006.01)
(52) U.S. Cl. .......................... 385/129; 385/14
(58) Field of Classification Search ................ 385/12, 385/129–132, 141–145, 147
    See application file for complete search history.

(56) References Cited

U.S. PATENT DOCUMENTS

| | | | |
|---|---|---|---|
| 5,184,192 A | 2/1993 | Gilby et al. | 356/246 |
| 5,416,879 A | 5/1995 | Liu | 385/125 |
| 5,444,807 A | 8/1995 | Liu | 385/125 |
| 5,561,523 A | 10/1996 | Blomberg et al. | 356/454 |
| 5,920,391 A | 7/1999 | Grasdepot et al. | 356/519 |
| 6,137,108 A | 10/2000 | DeThomas et al. | 250/399.07 |
| 6,199,257 B1 | 3/2001 | Munk et al. | 29/423 |
| 6,332,049 B1 | 12/2001 | Dasgupta | 385/12 |
| 6,542,231 B1 | 4/2003 | Garrett | 356/246 |
| 6,784,988 B2 | 8/2004 | Vijayakumar et al. | 356/244 |

(Continued)

OTHER PUBLICATIONS

Archambault, J-L, et al., "Loss calculations for antiresonant waveguides," *J. Lightwave Technol.*, 1993, 11(3), 416-423.

(Continued)

*Primary Examiner*—Kevin S Wood
(74) *Attorney, Agent, or Firm*—Woodcock Washburn LLP

(57) ABSTRACT

An optical waveguide is constructed so as to comprise a non-solid core layer surrounded by a solid-state material, wherein light can be transmitted with low loss through the non-solid core layer, and an electrical component is in fluid communication with the non-solid core layer. The electrical component controls movement of sample material through the non-solid core. The optical wave guide provides light confinement with structured dielectric materials. A presently preferred implementation of the invention employs anti-resonant reflecting optical waveguides (ARROWs or ARROW). Liquid-core waveguides may also be implemented using other dielectric confinement methods where the layers are periodic, such as Bragg mirrors, holey photonic crystal fiber, and omniguides.

111 Claims, 21 Drawing Sheets
(19 of 21 Drawing Sheet(s) Filed in Color)

U.S. PATENT DOCUMENTS

| | | | |
|---|---|---|---|
| 6,839,140 B1 | 1/2005 | O'Keefe et al. | 356/436 |
| 6,867,857 B2 | 3/2005 | Hobbs | 356/246 |
| 6,870,626 B2 | 3/2005 | Autrey et al. | 356/432 |
| 7,157,053 B2 * | 1/2007 | Hahn et al. | 422/82.09 |

OTHER PUBLICATIONS

Armenise, M. et al., "Modeling and design of a novel miniaturized integrated optical sensor for gyroscope systems," *J. Lightwave Technol.*, 2001, 19(10), 1476-1494.

Ashkin, A., "History of optical trapping and manipulation of small-neutral particle, atoms, and molecules," *IEEE Journal of Selected Topics in Quantum Electronics*, Nov.-Dec. 2000, 6(6), 841-856.

Bartenstein, M. et al., "Atoms and Wires: Toward Atom Chips," *IEEE Journal of Quantum Electronics*, 2000, 36(12), 1364-1377.

Benaissa, K. et al., "IC compatible optical coupling techniques for integration of ARROW with photodetector," *J. Lightwave Technology*, 1998, 16(8), 1423-1432.

Bernini, R. et al. "Silicon Micromachined Hollow Optical Waveguides for Sensing Applications", *IEEE J. Sel. Top. Quant. Elec.*, 2002, 8(1), 106-110.

Cantin, M. et al., "Remotely switched hollow-core antiresonant reflecting optical waveguide," *Opt. Lett.*, 1991, 16(22), 1738-1740.

Castro, A. et al., "Single-Molecule detection of specific nucleic acid sequences in unamplified genomic DNA," *Anal. Chem.*, 1997, 69, 3915-3920.

Chow, W.W. et al., "The ring laser gyro," *Rev. Mod. Phys.*, 1985, 57(1), 61-104.

Coldren, L.A. et al., *Diode Lasers and Photonic Integrated Circuits*, Wiley & Sons, Inc., 1995, Appendix 3, 428-440.

Datta A. et al. "Microfabrication and characterization of teflon AF-coated liquid core waveguide channels in silicon," *IEEE Sensors J.*, Dec. 2003, 3(6), 788-795.

Duguay, M.A., et al., "Antiresonant reflecting optical waveguides in $SiO_2$-Si multilayer structures," *Appl. Phys. Lett.*, 1986, 49(1), 13-15.

Fano, U., "Effects of Configuration Interaction on Intensities and Phase Shifts," *Phys. Rev.*, 1961, 124(6), 1866-1878.

Fill, E.E. et al., "Lasing without inversion via the lambda quantum-beat laser in the collision-dominated regime," *Opt. Comm.*, 1990, 77(1), 36-40.

Fink, Y. et al., "A dielectric omnidirectional reflector," *Science*, 1998, 282, 1679-1682.

Gifford, S.C. et al., "Parallel microchannel-based measurements of individual erythrocyte areas and volumes," *Biophysical J.*, 2003, 84, 623-633.

Gray, H.R. et al., "Coherent trapping of atomic populations," *Opt. Lett.*, 1978, 3(6), 218-220.

Gustavson, T.L. et al., "Precision Rotation measurements with an atom interferometer gyroscope," *Phys. Rev. Lett.*, 1997, 78(11), 2046-2049.

Gustavson, T.L. et al., "Rotation sensing with a dual atom-interferometer Sagnac gyroscope," *Class. Quantum Grav.*, 2000, 17, 2385-2398.

Hänsel, W. et al., "Bose-Einstein condensation on a microelectronic chip," *Nature*, 2001, 413, 498-501.

Harris, S.E. et al., "Nonlinear optical processes using electromagnetically induced transparency," *Phys. Rev. Lett.*, 1990, 64(10), 1107-1110.

Harris, S.E., "Lasers without inversion: interference of lifetime-broadened resonances," *Phys. Rev. Lett.*, 1989, 62(9), 1033-1036.

Imamoglu, A. et al., "Strongly interacting photons in a nonlinear cavity," *Phys. Rev. Lett.*, 1997, 79(8), 1467-1470.

Ivnitski, D. et al., "Biosensors for detection of pathogenic bacteria," *Biosensors & Bioelectronics.*, 1999, 14, 599-624.

Kasapi, A. et al., "Electromagnetically induced transparency: propagation dynamics," *Phys. Rev. Lett.*, 1995, 74(13), 2447-2451.

Kitching, J. et al., "Miniature vapor-cell atomic-frequency references," *Appl. Phys. Lett.*, 2002, 81(3), 553-555.

Koch, T.L. et al., "Antiresonant reflecting optical waveguides for III-V integrated optics," *Elec. Lett.*, 1987, 23, 244-245.

Kranz, M. et al., "A single-layer Silicon-on-Insulator MEMS gyroscope for wide dynamic range and harsh environment applications," *Proc. of the SPIE.*, 2001, 4559, 5-8.

Leistiko O. et al., "Integratd bio/chemical microsystems employing optical detection: the clip-on," *J. Micromech. Microeng.*, 1998, 8(2), 148-50.

Levene, M.J. et al., "Zero-mode waveguides for single-molecule analysis at high concentrations," *Science*, 2003, 299, 682-686.

Lim, H. et al., "A few deg/hr resolvable low noise lateral microgyroscope," *Technical Digest, MEMS 2002 IEEE International Conference*, 2002, 627.

Lin, S. et al., "Sensitivity analysis of the Sagnac-effect optical-fiber ring interferometer," *Applied Optics.*, 1979, 18(6), 915-931.

Little, B.E. et al., "Ultra-compact $Si-SiO_2$ microring resonator optical channel dropping filters," *IEEE Photonics Technology Letters*, 1998, 10(4), 549-551.

Liu, B. et al., "Wide tunable double ring resonator coupled lasers," *IEEE Photonics Technology Letters*, 2002, 14(5), 600-602.

Lou, H.J. et al., "Femtoliter microarray wells for ultrasensitive DNA/mRNA detection," *Instrumentation Science & Technology*, 2002, 30(4), 465-476.

Lukin, M.D. et al., "Intracavity electromagnetically induced transparency," *Opt. Lett.*, 1998, 23(4), 295-297.

Maltsev, V.P., "Scanning flow cytometry for individual particle analysis," *Review of Scientific Instruments*, 2000, 71(1), 243-255.

Mawst, L.J. et al., "Design optimization of Arrow-type diode lasers," *IEEE Photonics Technology Letters*, 1992, 4(11), 1204-1206.

Medina, M. et al., "Fluorescence correlation spectroscopy for the detection and study of single molecules in biology," *BioEssays*, 2002, 24, 758-764.

Miura, T. et al., "Novel phase-tunable three-dimensional hollow waveguides with variable air core," *IEEE Photonics Technology Letters*, 2003, 15(9), 1240-1242.

Miyagi, M. et al., "A proposal for low-loss leaky waveguide for submillimeter waves transmission," *IEEE Trans. on Microwave Theory and Tech.*, 1980, MTT-28(4), 398-401.

Nathan, A. et al., "Silicon integrated optic devices and micromechanical sensors based on Arrow," *Proceedings: SPIE—The International Society for Optical Engineering*, San Jose, California, Jan. 29, 1996, 2686, 2-16.

Padmabandu, G.G. et al., "Laser oscillation without population inversion in a sodium atomic beam," *Phys. Rev. Lett.*, 1996, 76(12), 2053-2056.

Paternostro, M. et al., "Generation of entangled coherent states via cross-phase-modulation in a double electromagnetically induced transparency regime," *Phys. Rev. A*, 2003, 67, 023811-1 thru 023811-15.

Patterson, S.G. et al., "Continuous-wave room temperature operation of bipolar cascade laser," *Electronics Letters.*, 1999, 35(5), 395-397.

Resch, K.J. et al., "Electromagnetically induced opacity for photon pairs," *Journal of Modern Optics*, 2002, 49(3/4), 487-502.

Rostovtsev, Y. et al., "Slow, ultraslow, stored, and frozen light," *Optics & Photonics News.*, 2002, 13, 44-48.

Rowe, C.H. et al., "Design and operation of a very large ring laser gyroscope," *Applied Optics*, 1999, 38(12), 2516-2523.

Russell, P., "Holey fiber concept spawns optical-fiber renaissance," *Laser Focus World*, 2002, 38, 77-82.

Saito, Y. et al., "Experimental trial of a hollow-core waveguide used as an absorption cell for concentration measurement of $NH_3$ gas with a $CO_2$ laster," *Opt. Lett.*, 1993, 18(24), 2150-2152.

Schmidt, H. et al., "Integrated optical spectroscopy of low-index gases and liquids using Arrow waveguides," *Integrated Photonics Research Conference*, 2003, 3 pages.

Schmidt, H. et al., "Giant Kerr nonlinearities using electromagnetically induced transparency," *Optics Letters*, 1996, 21(23), 1936-1938.

Schmidt, H. et al., "High-speed properties of a phase-modulation scheme based on electromagnetically induced transparency," *Optics Letters*, 1998, 23(13), 1007-1009.

Scully, M.O. et al., "High-sensitivity magnetometer based on index-enhanced media," *Phys. Rev. Lett.*, 1992, 69(9), 1360-1363.

Scully, M.O. et al., "Field-field and photon-photon interferometry," *Quantum Optics*, 1997, Chapter 4.1, 97-111.

Suzuki, K. et al., "Monolithically integrated resonator microoptic gyro on silica planar lightwave circuit," *J. of Lightwave Technology*, 2000, 18(1), 66-72.

Temelkuran, B. et al., "Wavelength-scalable hollow optical fibres with large photonic bandgaps for $CO_2$ laser transmission," *Nature*, 2002, 420, 650-653.

Wang, S-L. et al., "A Miniaturized Liquid Core Waveguide-Capillary Electrophoresis System with Flow Injection Sample Introduction and Fluorometric Detection Using Light-Emitting Diodes," *Anal. Chem.*, 2001, 73, 4545-4549.

Webb, W.W., "Fluorescence correlation spectroscopy: inception, biophysical experimentations, and prospectus," *Applied Optics*, 2001, 40(24), 3969-3983.

Woolley, A.T. et al., "Direct haplotyping of kilobase-size DNA using carbon nanotube probes," *Nature Biotechnology*, 2000, 18, 760-763.

Basche T et al., "Dynamical processes of single molecules as deduced from the fluorescence autocorrelation function," *Experimental Technique of Physics*, 1995, 41, 197-204.

Blanchard, S.C. et al., "tRNA dynamics on the ribosome during translation," *PNAS*, 2004, 101, 12893-12898.

Blanchard, S.C. et al., "tRNA selection and kinetic proofreading in translation," *Nature Structural & Molecular Biology*, 2004, 11(10), 1008-1014.

Culver, G.M., et al., "In vitro reconstitution of 30S ribosomal subunits using complete set of recombinant proteins," *Methods Enzymol.*, 2000, 318, 446-460.

Culver, G.M., et al., "Directed hydroxyl radical probing of RNA from iron(II) tethered to proteins in ribonucleoprotein complexes," *Methods Enzymol.*, 2000, 318, 461-475.

Deamer, D.W., et al., "Characterization of nucleic acids by nanopore analysis,", *Acc. Chem. Res.*, 2002, 35, 817-825.

Dorywalska, M. et al., "Site-specific labeling of ribosome for single-molecule spectroscopy," *Nucl. Acids Research*, 2005, 33(1), 182-189.

Duffy D.C., et al., "Rapid prototyping of microfluidic systems in poly(dimethylsiloxane)," *Analytical Chemistry*, 1998, 70, 4974-4984.

Frank, J., "The ribosome—a macromolecular machine par excellence," *Chemistry and Biology*, 2000, 7, R133-R141.

Grunwell, J.R. et al., "Monitoring the conformational fluctuations of DNA hairpins using single-pair fluorescence resonance energy transfer," *J. Am. Chem. Soc.*, 2001, 123, 4295-4303.

Guijt , R.M. et al., "New approaches for fabrication of microfluidic capillary electrophoresis devices with on-chip conductivity detection," *Electrophoresis*, 2001, 22, 235-241.

Hadley, G.R., et al., "Bragg fiber design for linear polarization," *Opt. Lett.*, 2004, 29(8), 809-811.

Haran, G., "Single-molecule fluorescence spectroscopy of biomolecular folding," *J. Phys.*, 2003, 15, R1291-R1317.

Hartz, D. et al., "Selection of the initiator tRNA by *Escherichia coli* initiation factors," *Genes Dev.* 1989, 3, 1899-1912.

Hollars C.W., et al., "Controlled non-classical photon emission from single conjugated polymer molecules," *Chemical Physics Letters*, 2003, 370, 393-398.

Lancaster, L., et al., "The location of protein S8 and surrounding elements of 16S rRNA in the 70S ribosome from combined use of directed hydroxyl radical probing and X-ray crystallography," *RNA*, 2000, 6, 717-729.

Li, J. et al., "Ion-beam sculpting at nanometer length scales," *Nature*, 2001, 412, 166-169.

Lieberman, K.R., et al., "The 23 S rRNA environment of ribosomal protein L9 in the 50 S ribosomal subunit," *J Mol Biol.*, 2000, 297, 1129-1143.

McDonald J.C., et al., "Poly(dimethylsiloxane) as a material for fabricating microfluidic devices," *Accounts of Chemical Research*, 2002, 35(7), 491-499.

Monahan J., et al., "A method for filling complex polymeric microfluidic devices and arrays," *Analytical Chemistry*, 2001, 73, 3193-3197.

Noller, H.F. et al., "Translocation of tRNA during protein synthesis," *FEBS Letters*, 2002, 514, 11-16.

Peeni, B.A et al., "Planar thin film device for capillary electrophoresis," *Lab on a Chip*, 2005, 5, 501-505.

Schmidt, H. et al., "Hollow-core waveguides and 2-D waveguide arrays for integrated optics of gases and liquids," *IEEE Journal of Selected Topics in Quantum Electronics*, 2005, 11(2), 519-527.

Wilson, K.S., et al., "Functional sites of interaction between release factor RF1 and the ribosome," *Nat Struct Biol.*, 2000, 7(10), 866-870.

Yeh, P. et al., "Electromagnetic propagation in periodic stratified medial. I. General theory.," *J. Opt. Soc. Am.*, 1977, 67(4), 423-438.

Yin, D. et al., "Integrated optical waveguides with liquid cores," *Applied Physics Letters*, 2004, 85(16), 3477-3479.

Yin, D et al., "Integrated Arrow waveguides with hollow cores," *Optics Express*, 2004, 12(12), 2710-2715.

Yusupov, M., et al., "Crystal structure of the ribosome at 5.5 Å resolution," *Science*, 2001, 292, 883-896.

Kneipp, K. et al., "Surface-enhanced and normal stokes and anti-stokes Raman Spectorscopy of single-walled carbon nanotubes," *Phys. Rev. Lett.*, 2000, 84, 3470-3473.

Schwartz et al., "Capillary electrophoresis with laser-induced fluorescence detection of PCR fragments using Thiazole Orange," *Anal. Chem.*, 1992, 64, 1737-1740.

Srinivasan, et al., "Electrophoretic separations of polymerase chain reaction-amplified DNA fragments in DNA typing using a capillary electrophoresis-laser induced fluorescence system," *Journal of Chromatography A*, 1993, 652, 83-91.

Woolley et al., "Ultra-high-speed DNA fragment separations using microfabricated capillary array electrophoresis chips," *Proc. Natl. Acad. Sci. USA*, 1994, 91, 11348-11352.

Yin, D. et al., "Highly efficient fluorescence detection in picoliter volume liquid-core waveguides," *Appl. Phys. Lett.*, 2005, 87, 211111.

* cited by examiner

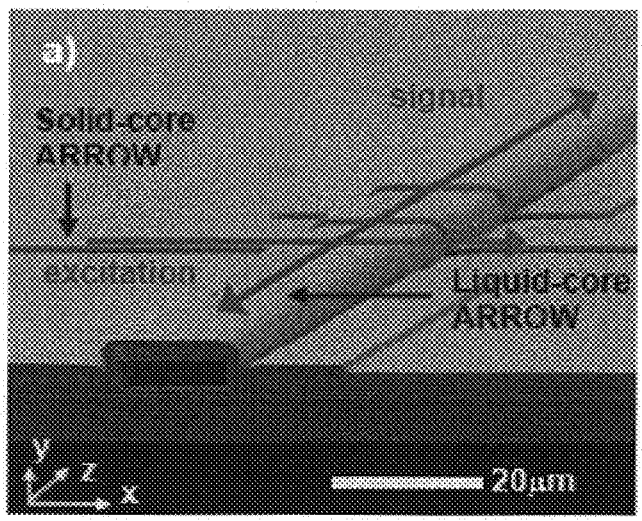
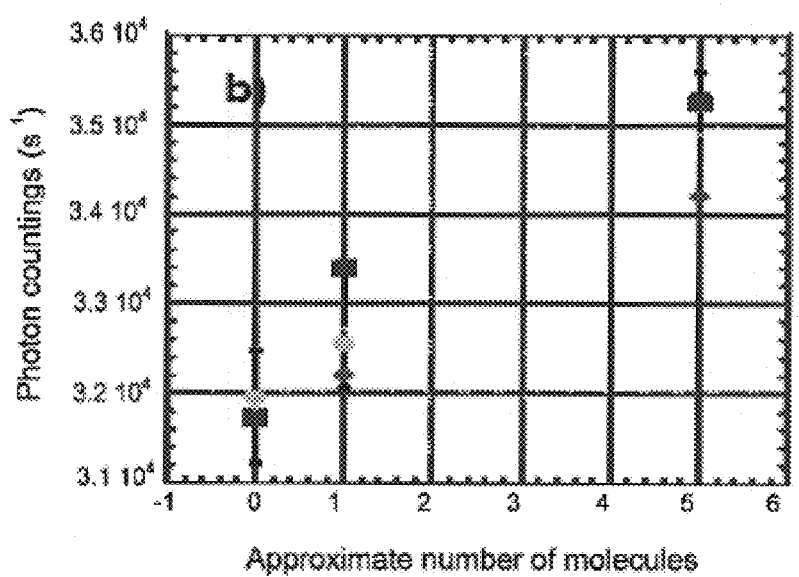
Figure 1

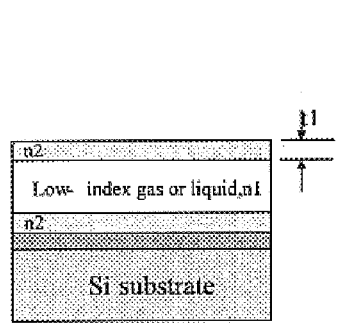
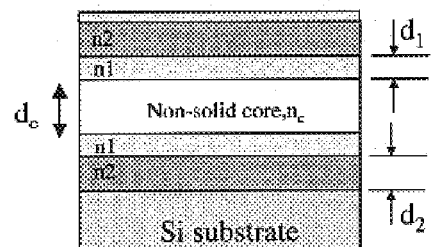
FIGURE 8(a)   FIGURE 8(b)
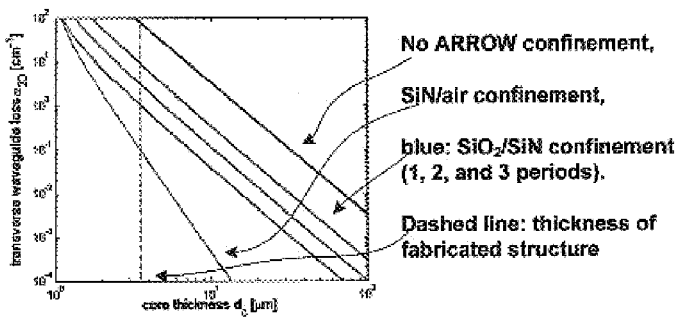
FIGURE 8(c)
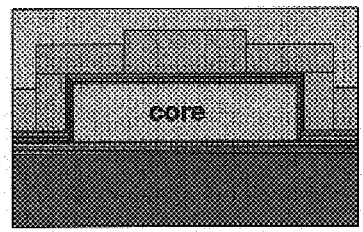
FIGURE 8(d)   FIGURE 8(e)
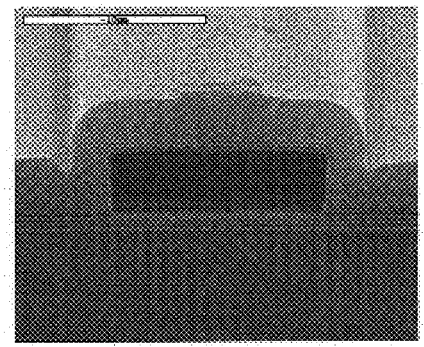
FIGURE 8(f)

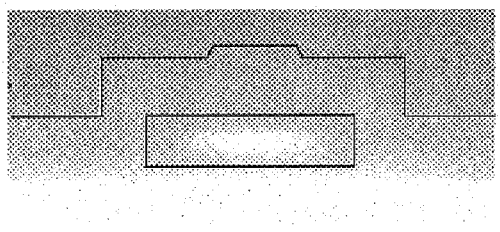
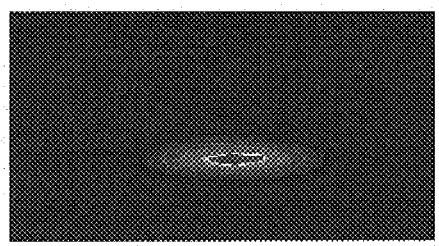
FIGURE 8(g)   FIGURE 8(h)
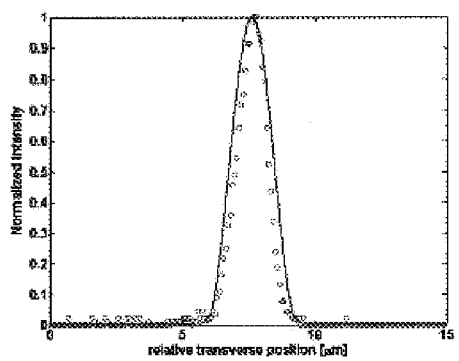
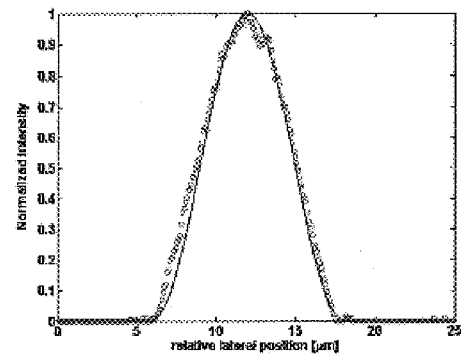
FIGURE 8(i)   FIGURE 8(j)
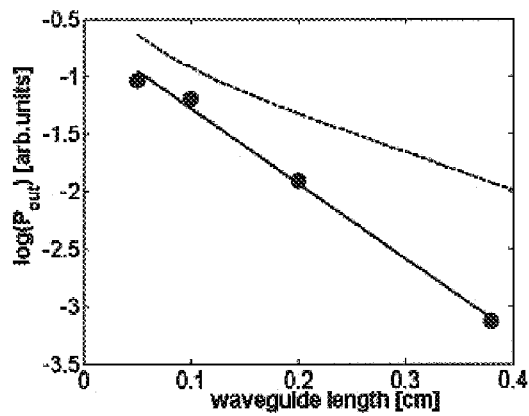
FIGURE 8(k)

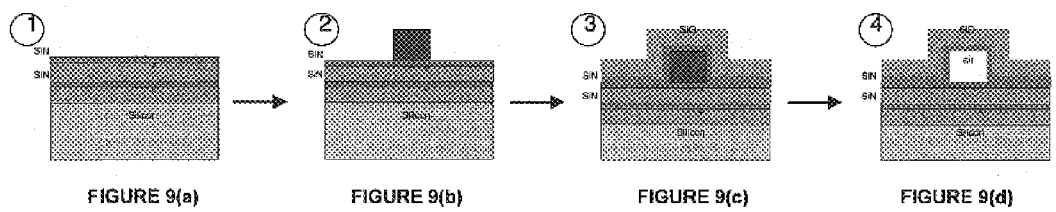

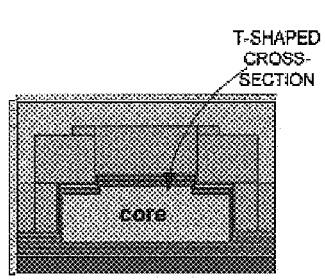
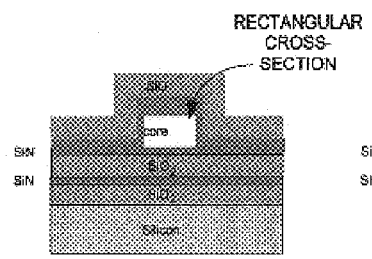
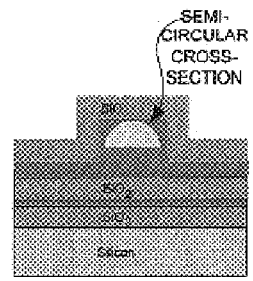
FIGURE 10(a)  FIGURE 10(b)  FIGURE 10(c)
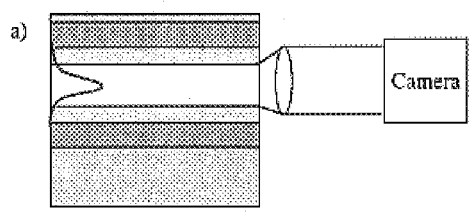
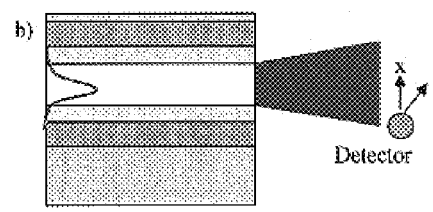
FIGURE 11(a)  FIGURE 11(b)
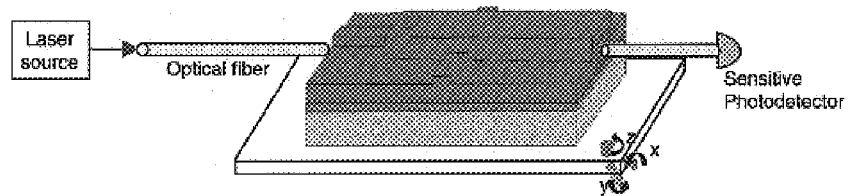
FIGURE 12

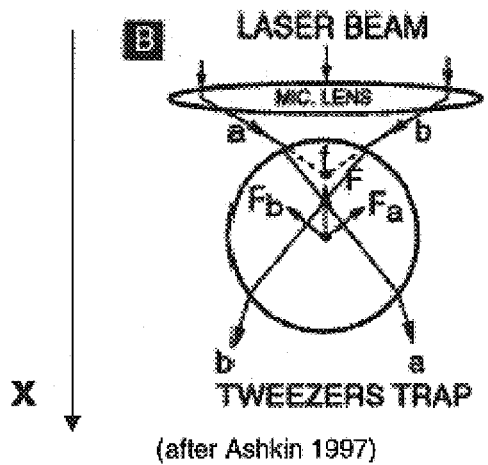
FIGURE 14(a) (PRIOR ART)
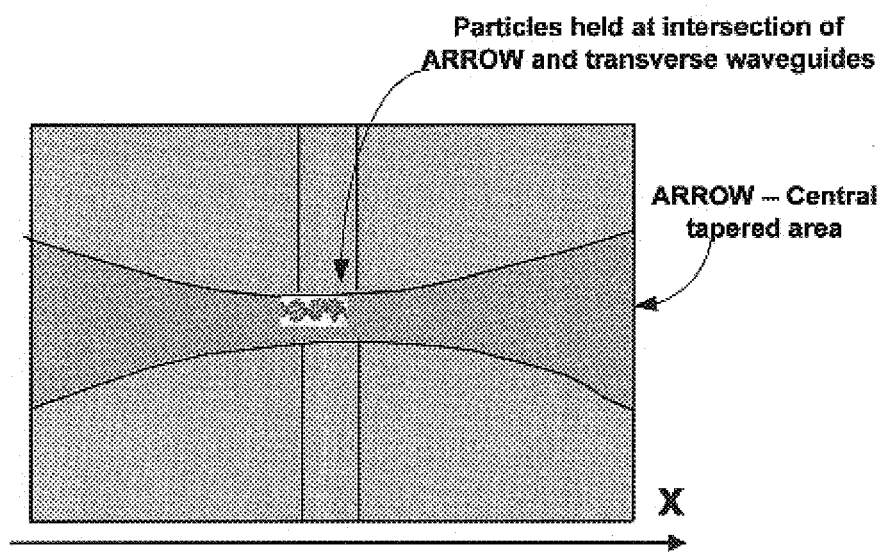
FIGURE 14(b) (TOP VIEW OF ARROW WAVEGUIDE)

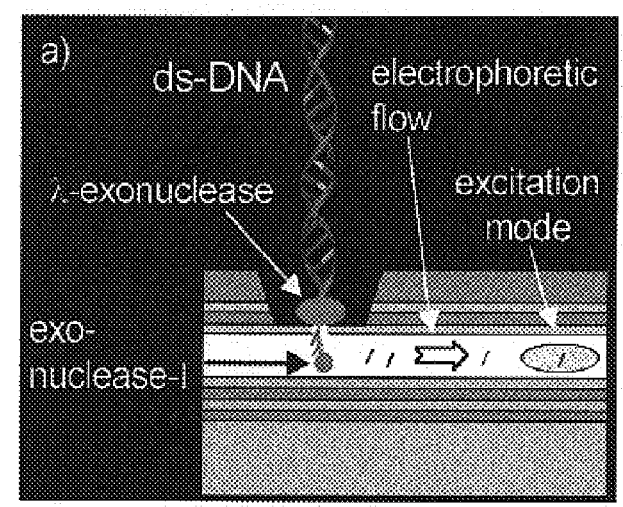
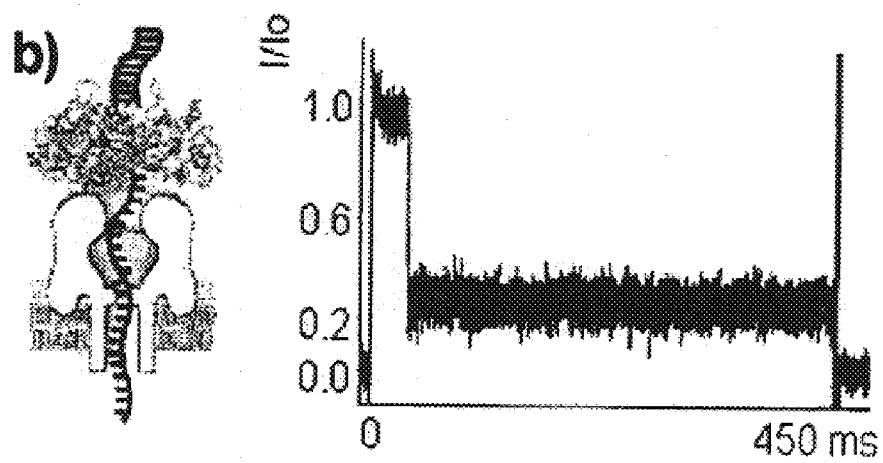
Figure 28

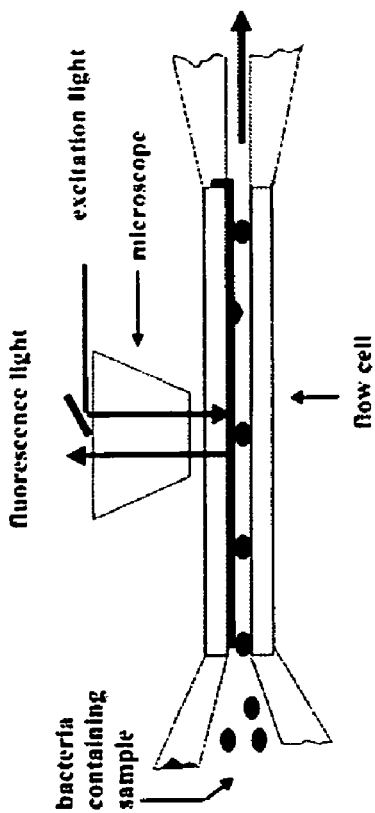
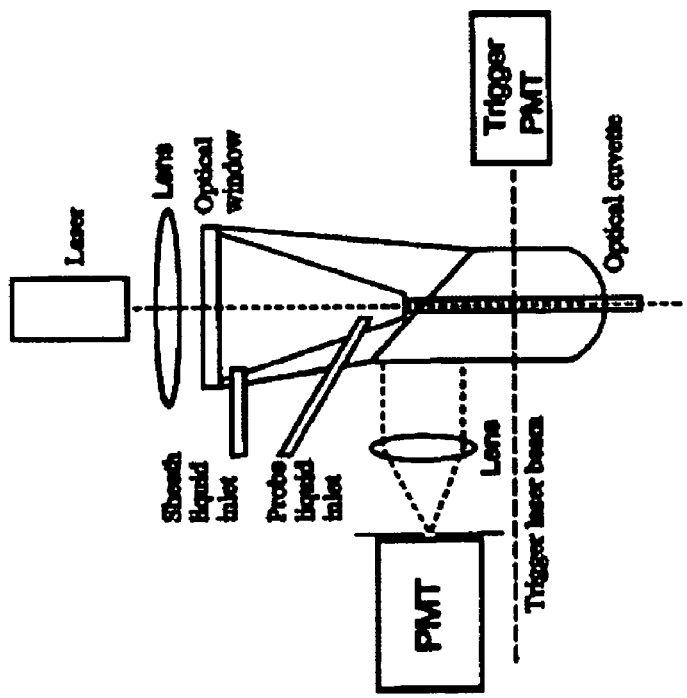
Figure 29

INTEGRATED ELECTRICAL AND OPTICAL SENSOR FOR BIOMOLECULE ANALYSIS WITH SINGLE MOLECULE SENSITIVITY

CROSS REFERENCE TO RELATED APPLICATIONS

This application is a continuation-in-part of U.S. application Ser. No. 11/251,014, filed Oct. 14, 2005, which is a continuation-in-part of U.S. application Ser. No. 10/868,475, filed Jun. 15, 2004, which claims the benefit of the filing date of U.S. Provisional Application No. 60/479,376, filed Jun. 16, 2003, which are hereby incorporated by reference in their entirety.

TECHNICAL FIELD

The present invention relates generally to the field of integrated optics, and more particularly to an optical waveguide comprising a non-solid core layer surrounded by a solid-state material, wherein light can be transmitted with low loss through the non-solid core layer, and an electrical component is in fluid communication with the non-solid core layer. The electrical component controls movement of sample material through the non-solid core. The optical wave guide provides light confinement with structured dielectric materials. A presently preferred implementation of the invention employs anti-resonant reflecting optical waveguides (ARROWs or ARROW). Liquid-core waveguides may also be implemented using other dielectric confinement methods where the layers are periodic, such as Bragg mirrors, holey photonic crystal fiber, and omniguides. ARROWs have a number of implementation advantages when integrated on a chip.

BACKGROUND

Our invention provides a practical way to extend the field of integrated optics to non-solid waveguide core materials. That is, we describe a way for guiding light on a chip through non-solid materials such as gases and liquids. Light can not only interact with these materials at the location of the active elements in the integrated device, the connections ("optical wires") between elements can also occur through the non-solid materials. Before we explain certain background information relevant to our invention, it should be noted that, although we focus much attention to biomedical applications, the present invention is not limited to any specific application, biomedical or otherwise. The present invention may be applied to a broad range of problems, including but not limited to: the sensing of gases and liquids; single molecule spectroscopy (e.g., fluorescence); quantum optics and quantum information processing; optical measurements of extremely small volumes of gases and liquids; optical tweezers for manipulating tiny (microscopic) particles using light forces; implantable biomedical sensors, etc. Accordingly, except as they may be expressly so limited, the scope of protection of the claims at the end of this specification is by no means limited to the specific applications described herein.

Currently, there are a number of optical methods being used to improve human health and answer health-related scientific questions. These include both applications which are already well advanced (e.g., cell flow cytometry; Maltsev, V. P., Rev. Sci. Inst. 71, 243, 2000; H. M. Shapiro, "Practical Flow Cytometry", Wiley & Sons, 3rd Edition, 1995; Ivnitski, D. et al., Biosensors and Bioelectronics 14, 599, 1999; blood measurements; Gifford, S. C. et al., Biophysical Journal 84, 623, 2003) as well as very fundamental questions regarding the human body (e.g., basic understanding and counting of single DNA molecules. Levene, M. J. et al., Science 299, 682, 2003). Such single molecule studies are carried out to improve drug screening, mRNA expression profiling, and DNA sequencing. Castro, A., et al., Anal. Chem., 69, 3915, 1997; Woolley, A. T. et al., Nature Biotechnology 18, 760, 2000. At the same time, there is a continuing trend to increase the sensitivity of biomedical sensors and imaging methods, down to very small sample volumes (Webb, W. W., Applied Optics 24, 3969, 2001; Lou, H. J. et al., Instrumentation Science and Technology 30, 465, 2002) and individual molecules (DNA). Another area where exquisite sensitivity is required is detection of toxic substances in the gas phase (e.g., in air). We will describe below some specific examples of state-of-the-art methodologies that are currently being used, and describe their performance and limitations. Then we will describe our novel approach with emphasis on how existing problems are addressed and solved.

(i) DNA Fluorescence with Single Molecule Resolution

There are a couple of methods for optical measurements on single molecules. A popular one is to observe them using diffraction-limited optics (Medina, M. et al., *Bioessays* 24, 758, 2002). The principle of one technique—fluorescence correlation spectroscopy—is shown in FIG. 3(*a*). Problems associated with this method include the fact that only extremely small volumes on the order of fl are tolerable, and more importantly, that such setups are bulky in nature and cannot be scaled readily to multiple sample volumes.

A potentially significant improvement to some of these issues has recently been made by Levene et al. (Levene, M. J. et al., *Science* 299, 682, 2003), who developed a detection method with single molecule sensitivity based on evanescent coupling of light from molecules trapped in sub-micron sized holes in metal films. The principle is shown in FIG. 2(*b*) where enzymatic synthesis of double-stranded DNA by DNA polymerase using fluorescently tagged nucleotide analog coumarin-dCTP was measured.

Using such zero-mode waveguides, the observation volume can be increased to the micromolar level. However, while this method is clearly ingenious, it can be seen from FIG. 2(*b*) that the setup is still rather cumbersome and involves optical paths for excitation and detection that are perpendicular to the sample plane. The metal film contains a large number of these zero-mode waveguides, which results in large parallelism. However, since the fluorescence is collected through a microscope objective, a large number of these holes are interrogated simultaneously and deliberate readout from a single hole is impossible. In addition, evanescent waveguide coupling is a concept that is currently pursued by many groups to couple optical signals into waveguides. However, it is highly inefficient as it relies on detection of exponentially decaying electric field values of the fluorescence signal. As a result, no transport of the optical signal through a waveguide or all-optical post-processing is possible.

(ii) Flow Cytometry of Small Volumes

Another area in which optical interactions with a liquid sample containing biological material are being studied is flow cytometry. This field is rather well developed and an advanced setup capable of individual particle analysis is shown in FIG. 4(*a*). Maltsev, V. P., *Rev. Sci. Inst.* 71, 243, 2000.

In this case, a microchannel containing the specimen with a width of 10 μm is used. A laser is sent into this channel and fluorescence is detected perpendicular to the excitation direction. The important facts to note are that no waveguiding within the microcuvette is involved, measurements of multiple channels is impossible with this setup and the whole setup is composed of bulk optics.

Another example for a generic flow cytometry setup is shown in FIG. 4(b). In FIG. 4(b), a liquid sample containing potentially pathogenic bacteria is passed through a flow cell and the specimen is excited using a microscope objective in the perpendicular direction. This arrangement brings with it significant loss of the optical signal due to multiple interfaces between the sample space and the end of the microscope objective. In addition, only one channel can be excited this way as the focal depth of the excitation spot is very small and the excitation beam diverges quickly after it passes the flow cell. Leistiko O and Jensen P F. [Conference Paper] *IOP Publishing. Journal of Micromechanics & Microengineering*, 8, 148-50, 1998 describe another realization of a microfluidic channel system for biological and biochemical applications. There, optical fibers are placed in etched grooves on a silicon substrate and covered with a pyrex slide. The light from the optical fibers is coupled into integrated waveguides in the silicon. However, they intersect an ordinary microcapillary which again leads to significant coupling losses into and out of the capillary leading to a coupling efficiency of only a few percent.

In light of the limitations and problems described above, and as discussed in greater detail below, we have invented a new approach to develop a planar integrated platform for such optical measurements with high sensitivity and the potential for massive parallelism. A presently preferred implementation of our invention is based on ARROW waveguides. Miyagi, M. et al., *IEEE Trans. On Microwave Theory and Tech.* 28, 298, 1980; Duguay, M. A., et al., *Appl. Phys. Lett.* 49, 13, 1986. We will first describe the principle behind these waveguides and then explain several ways in which they may be used.

In conventional waveguides, light is guided in a medium with higher refractive index than its surroundings (e.g., silica fiber/air). When the refractive index situation is reversed (e.g., in microcapillaries), light cannot be guided in the central low-index region (core) and will leak out as shown in FIG. 5(a). A solution to this problem is to prevent the transverse components of the propagation vector from leaking out. This can be accomplished by adding Fabry-Perot reflectors in the transverse direction as is shown in FIG. 5(b). The high-index layers will reflect most of the light propagating in the transverse direction (vertical direction in FIGS. 3(a), (b)). The thickness t of the high-index cladding layer is chosen correctly to yield the desired interference.

It is important to note that these structures are well-known in optoelectronics and photonics where they have mainly been used as design tools for high-power and cascade lasers. Mawst, L. J. et al., *IEEE Phot. Technol. Lett.* 4, 1204, 1992; Patterson, S. G. et al., *Electronics Letters* 35, 395, 1999. In all applications, however, the ARROW waveguides were made using only solid-state semiconductor or dielectric materials. We are interested in ARROW waveguides where the low-index core is liquid or gaseous. Schmidt, H. et al., *Integrated Photonics Research Conference*, Washington, D.C., 2003. It should also be pointed out that light guiding in low-index media is also possible using photonic bandgap structures (Joannopoulus, J. D. et al., "Photonic crystals," Princeton University Press, 1995). However, such structures are extremely complicated to fabricate and cannot be used for some of the applications of interest here. They also rely on structures with long range periodicity which is not required for ARROW structures. In addition, fabrication of hollow core ARROW waveguides has been proposed using a different fabrication method. R. Bernini et al., *IEEE J. Sel. Top.*

*Quant. Elec.* 8, 106-110, 2002. Finally, a method for index-guiding through aqueous liquids in large diameter (several 100 microns) Teflon waveguides was demonstrated. (Datta A et al., [Journal Paper] *IEEE Sensors Journal*, 3, 788-95, 2003). Single-mode propagation and light confinement in gases is not possible with this approach.

SUMMARY

In an embodiment of the invention, an optical waveguide is constructed so as to comprise a non-solid core layer surrounded by a solid-state material, and an electrical component that may be placed in fluid communication with a sample material/analyte in the non-solid core layer. The electrical component may be employed to control movement of the sample material or analyte within the sample material through the non-solid core. The electrical component can be an electrophoretic component or an electroosmotic component. The analyte within the sample material can include, but is not limited to, a nucleic acid molecule, a protein molecule, or an amino acid molecule. The analyte can be a single molecule or a single particle. The nucleic acid molecule, protein molecule, or amino acid molecule can be separated from a mixture in the sample material. In a detailed aspect, a single nucleic acid molecule, a single protein molecule, a single amino acid molecule or a single particle can be separated from the mixture. The single nucleic acid molecule, single protein molecule, single amino acid molecule or single particle can be detected within the optical waveguide. The single particle in the sample material can be one cell or one viral particle. In particular, unlike the micromachined structure disclosed by Bernini, et al., in "Silicon Micromachined Hollow Optical Waveguides for Sensing Applications", supra, the optical waveguide includes a substrate and multiple layers of solid state material deposited on the substrate, and a non-solid core extending through at least one of the multiple layers. The substrate can be made of Silicon (Si) or other solid material. The waveguides in question could be made on different semiconductor substrates but also on a smooth metal, ceramic, or plastic surface.

The non-solid core may be used to contain a sample material whose light transmission, absorption, and/or interference characteristics are to be measured. The sample may have an index of refraction which is lower than the index of refraction of the surrounding solid-state material, and light can be transmitted with low loss through the non-solid core layer and sample material.

The optical waveguide is provided in which the electrical component can be a first electrode and a second electrode applying a current across a length of the non-solid core. In a detailed aspect, the optical waveguide further comprises a first reservoir and a second reservoir at opposite ends of the non-solid core in fluid communication with the non-solid core, the first reservoir in fluid communication with the first electrode and the second reservoir in fluid communication with the second electrode. In a detailed aspect, the electrodes are microelectrodes integrated on the substrate. The electrodes include, but are not limited to, platinum or silver/silver chloride.

The optical waveguide can further comprise a detector of light transmission, absorption, and/or interference characteristics. The detector can be an optical detector integrated with the optical waveguide on the substrate. A single nucleic acid molecule, a single protein molecule, a single amino acid molecule or a single particle from the sample material can be detected by the optical detector. The detector includes, but is not limited to, a fluorescence detector, a light detector or a Raman scattering detector.

The optical waveguide can further comprise a nanopore or micropore in fluid communication with the non-solid core, wherein a detailed aspect, the nanopore or micropore is configured to limit passage of a sample material through the nanopore or micropore to a single molecule or particle at a time.

The optical waveguide can further comprise one or more antiresonant reflecting layers adjacent to the non-solid core, whereby light is substantially prevented from leaking out of the core in a transverse direction. The one or more antiresonant reflecting layers can comprise a Fabry-Perot reflector adjacent to the non-solid core. The substrate can comprise silicon (Si) and the multiple layers comprise $SiO_2$ and SiN. The optical waveguide can further comprise the non-solid core having an index of refraction which is lower than the index of refraction of the surrounding solid-state material, and wherein light can be transmitted with low loss through the non-solid core. The optical waveguide can be generally structured as an anti-resonant reflecting optical waveguide (ARROW). In a detailed aspect, the one or more antiresonant reflecting layers is a Fabry-Perot reflector adjacent to the non-solid core.

The optical waveguide can further comprise a perpendicular waveguide portion for use in injecting light into the non-solid core for measuring fluorescence characteristics associated with a sample material. The cross section of the non-solid core can include, but is not limited to, a substantially square cross-section, a substantially rectangular cross-section, or a substantially arched cross-section. The optical waveguide can further comprise a sample-injection port in fluid communication with the non-solid core for injecting the sample material into the non-solid core. In one aspect, the sample injection port is oriented substantially perpendicular with respect to a longitudinal axis of the non-solid core. In a further aspect, the sample injection port is oriented above the non-solid core.

The present invention may also be embodied in an optical waveguide generally structured as an anti-resonant reflecting optical waveguide (ARROW), comprising a substrate and multiple layers of solid state material disposed on the substrate, and a non-solid core extending through at least one of the multiple layers, wherein the non-solid core has an index of refraction which is lower than the index of refraction of the surrounding solid-state material, and wherein light can be transmitted with low loss through the non-solid core, a Fabry-Perot reflector adjacent to the non-solid core, for substantially preventing light from leaking out of the core in a transverse direction, a perpendicular waveguide portion for use in injecting light into the non-solid core for measuring fluorescence characteristics associated with the sample material, a sample-injection port in fluid communication with the non-solid core for injecting a sample fluid into the non-solid core, the sample injection port being oriented substantially perpendicular with respect to a longitudinal axis of the non-solid core, and an electrical control component in fluid communication with the non-solid core to control movement of an analyte in the sample fluid through the non-solid core.

In accordance with another aspect of the invention, a measurement system is provided comprising an optical waveguide comprising a channel surrounded by a solid-state material, including a Fabry-Perot reflector adjacent to the channel, whereby light is substantially prevented from leaking out of the channel in a transverse direction, a perpendicular waveguide portion for use in injecting light into the channel, means for injecting into the channel an analyte in a sample fluid, an electrical component in fluid communication with the non-solid core to control movement of the analyte through the non-solid core, and means for measuring selected optical and electrical properties associated with the analyte in the sample.

A system for making parallel optical and electrical measurements is provided comprising an optical waveguide comprising a generally planar solid-state material and a plurality of parallel channels within the solid-state material, including a Fabry-Perot reflector adjacent to each channel, whereby light injected into the channels is substantially prevented from leaking out of the channels in a transverse direction; a port for injecting through each of the channels a sample material; a perpendicular waveguide portion for use in injecting light into the channels in a direction which is generally perpendicular to the orientation of the channels; means for measuring selected optical and/or electrical properties associated with an analyte in the sample material; and an electrical component in fluid communication with the channels to control movement of the analyte in the sample material through the plurality of parallel channels.

Other features and advantages of the present invention are described below.

BRIEF DESCRIPTION OF THE DRAWINGS

The file of this patent contains at least one drawing/photograph executed in color. Copies of this patent with color drawings/photographs will be provided by the Office upon request and payment of the necessary fee.

FIG. 1 comprises parts (a) and (b). FIG. 1(a) depicts an SEM image of intersection of solid core ARROW with a liquid core ARROW; and FIG. 1(b) depicts a graph of average number of photon counts versus number of molecules in excitation volume (symbols: different experimental runs).

FIG. 8(a) depicts a single-ARROW structure in which only the first cladding layer (thickness t1) is antiresonant and provides guiding. FIG. 8(b) depicts a double-ARROW structure in which both the first and second cladding layers (d1 and d2) are antiresonant, resulting in much better waveguiding.

FIG. 8(c) is a graph showing transverse mode loss for various waveguide types.

FIGS. 8(d) and 8(e) show waveguide cross-sections for 3D confinement, with 8(d) showing lateral confinement by ARROW layers and 8(e) showing lateral confinement by effective index guiding due to a ridge in top layer.

FIG. 8(f) is an SEM image of a fabricated hollow-core ARROW waveguide with core dimensions are 12 μm by 3.5 μm with a 0.57 μm high and 5 μm wide ridge on top.

FIG. 8(g) depicts an output facet image of a mode propagating in a hollow ARROW waveguide, with black lines outlining the sample for clarity. FIG. 8(h) shows a near-field intensity mode profile.

FIGS. 8(i) and 8(j) provide a comparison of observed transverse and lateral mode profiles (circles) with theoretical calculation (lines).

FIG. 8(k) is a graph of waveguide loss versus waveguide length. Circles: experiment, line: exponential fit.

FIGS. 9(a), 9(b), 9(c) and 9(d) depict steps of a fabrication process in accordance with the present invention.

FIGS. 10(a), 10(b) and 10(c) respectively depicts structures like those depicted in FIGS. 9(a), 9(b), 9(c) and 9(d) but showing that the non-solid core may be made with different cross-sectional shapes, including T-shaped, rectangular, and semi-circular.

FIGS. 11(a) and 11(b) depict waveguide characterization setups. FIG. 11(a) shows a near-field setup, where the emission at the output facet is imaged onto a camera. FIG. 11(b) shows a far-field setup, where the waveguide emission is detected several inches away from the facet (far-field) and recorded by scanning a detector perpendicular to the propagation direction.

FIG. 12 depicts an absorption measurement setup for an ARROW waveguide, wherein an optical connection to the sample is made with conventional fiber optic techniques within the wafer plane.

FIGS. 14(a) and 14(b) depict how the present invention may be employed to provide integrated optical tweezers.

FIGS. 28(a) and 28(b) illustrate a) DNA sequencing with nanopore device. b) Left: Hemolysin nanopore with λ-exonuclease. Right: Prolonged current blockade in presence of λ-exonuclease.

FIG. 29 illustrates flow cytometry setups after V. P. Maltsev, *Rev. Sci. Inst.*, 71, 243, 2000 and D. Ivnitski et al., *Biosensors and Bioelectronics*, 14, 599, 1999. In both cases, light cannot be guided along the liquid channel and is detected in the perpendicular direction.

DETAILED DESCRIPTION OF ILLUSTRATIVE EMBODIMENTS

Overview

Currently, cutting edge optical studies of biological agents such as DNA molecules or cells do not take advantage of the established technologies that have made optoelectronic and photonic integrated circuits so successful. Optical setups for biomedical applications typically involve bulky three-dimensional setups and often times the use of microscope objectives for excitation and/or collection. The main reason behind this fact is the inability to guide light through the media in which the cells and molecules are hosted (typically aqueous solutions or gas phase), as these media have lower refractive indices than the surrounding solid-state material.

Here, we present the invention of a radically different approach to creating an experimental platform for optical studies on non-solid-state materials. By using specially designed multi-layer optical waveguides, it is possible to guide light through low-index media over macroscopic distances which will enable optical devices with both improved and novel capabilities. A further aspect is an apparatus for simultaneous optical and electrical sensing with single-molecule sensitivity or single cell sensitivity based on integration of biological and synthetic nanopores or micropores with optical waveguides.

Some novel aspects of this approach compared to state-of-the-art techniques include:

- low-loss guiding of light inside a narrow channel of low-index media (gaseous or liquid), e.g., a non-solid core, on a semiconductor chip. Low-index in this context means that the refractive index of the sample material is less than any of the indices of the solid-state host material.
- Ability to guide light in the same volume as the low-index material. This allows for transmission, absorption or interference measurements over macroscopic distances.
- Ability to discriminate/filter selective wavelengths along the sample volume. This results from the fact that the waveguide is optimized for a desired wavelength range.
- Entirely planar technology for high sensitivity optical measurements compatible with fiber-optic technology.
- Massive parallelism for multiple measurements on a single chip.
- Potential for further integration with additional optical elements such as photo detectors on the same chip.
- Ability for optical measurements on microchannels of an order of magnitude smaller dimension.
- Specific methods to fabricate hollow-core ARROW waveguides based on sacrificial core layers.
- Platform for realizing large nonlinear phase shifts between light signals using EIT in atoms, e.g., Rb.
- System for fluorescence detection in two-dimensional interconnected solid and liquid-core ARROW waveguides. Single molecule sensitivity and electrical control of analyte flow through the liquid core ARROW waveguides has been demonstrated for deterministic generation of optical signals with ultra-high sensitivity.

Figure 13:
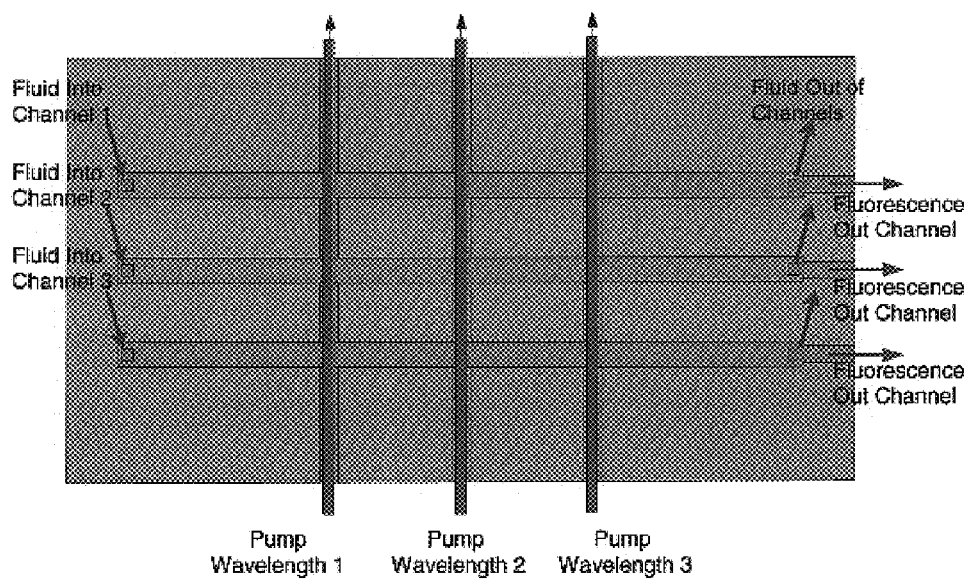
FIG. 13 depicts a top sectional view of an exemplary (3×3 array) parallel optical measurement system based on ARROW waveguide technology in accordance with the present invention.

Shown in the drawings are two images that show an implementation of the invention on a single device level as well as in a highly integrated setting for parallel measurements. These two implementations are shown in FIGS. 6 and 13, respectively.

Figure 6A:
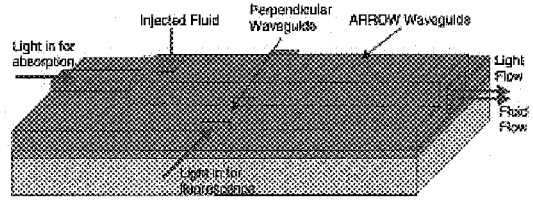
FIGS. 6(a), (b), and (c) depict an integrated optical measurement platform based on ARROW waveguides, in accordance with the present invention.
Figure 6B:
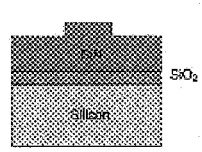
Figure 6C:
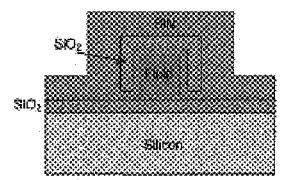

FIGS. 6(a)-(c) show our target sample design using integrated ARROW waveguides that illustrates a number of important advantages and novelties. By using this concept, we will achieve the following improvements over current state-of-the art methods: We can rely on light coupling and collection in the plane of the substrate leading to a compact scalable layout, higher coupling efficiencies of light emitted from a radiating dipole into the waveguide mode and consequently improved sensitivities. We can utilize fiber-optic waveguide coupling into the structures, which is well-developed in optoelectronics and photonics. We will be able to guide light along with the sample inside the chip, which will allow for completely novel experiments such as absorption measurements along the channel as well as simultaneous fluorescence detection and filtering along the direction of the sample flow. Importantly, we will gain the potential for parallel measurements on multiple channels since the excitation beam propagates in a waveguide mode—not as a Gaussian beam with a single focus as is the case in the approaches described above. Finally, ARROW waveguides will permit measurements on smaller volumes for flow cytometry.

Figure 7A:
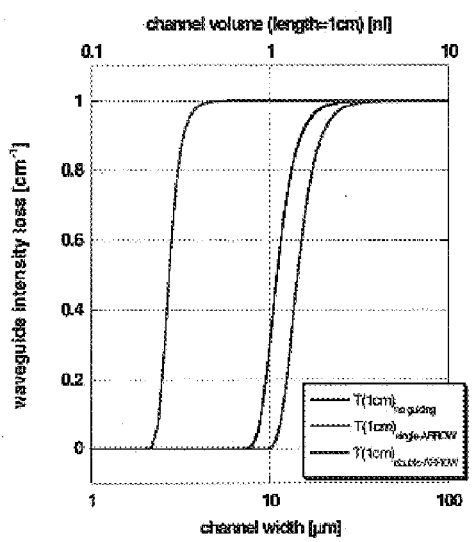
FIGS. 7(a) and (b) show comparisons of optical loss and transmission, respectively, in low-index liquids compared to ARROW structures, illustrating that ARROW structures lead to extremely low loss and can be used with smaller sample volumes.
Figure 7B:
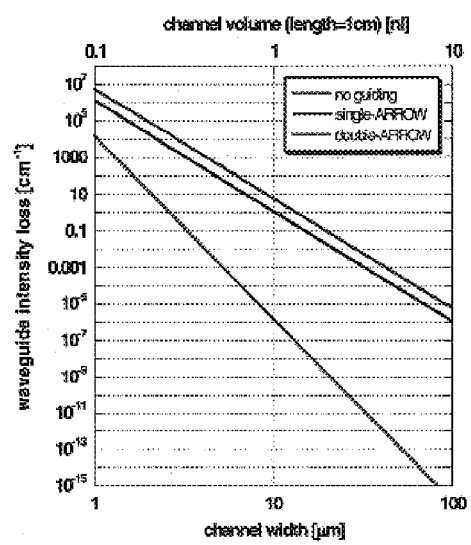

The dramatic effect on flow cytometry is illustrated by FIG. 7(a) and (b), which compare optical guiding in a conventional microfluidic channel or capillary with two types of ARROW structures to be described in more detail below. FIG. 7(a) shows the propagation loss in $cm^{-1}$ in a structure versus core dimension a (bottom axis) and resulting sample volume (top axis, channel length: 1 cm). It can be seen that losses in a double-ARROW structure are several orders of magnitude lower than in a regular microchannel. As shown in FIG. 7(b), this leads to significantly improved waveguide transmission down to the micron range, which will be sufficient for detecting any bacteria and other cells with dimensions of a few microns.

Single molecule studies play an increasingly important role in developing our understanding of biosystems on the nanoscale. The ability to isolate and probe individual biomolecules is desirable for several reasons. It allows access to intrinsic molecular behavior and functionality by eliminating ensemble effects due to statistical averaging. It also enables detection, identification, and analysis of the smallest possible quantities and therefore molecular sensing with ultimate sensitivity in environments with minute amounts of sample material. Single molecules can be studied using both electrical and optical techniques. Electrical current blockades caused by molecules transversing a nanoscopic pore in a membrane provide a means to study individual DNA and RNA molecules. Fluorescence and Raman spectroscopy are well-developed optical techniques to probe single molecules. A combination of both electrical and optical methods in a single device integrated on a semiconductor chip is an intriguing possibility that can significantly advance our knowledge of molecular processes on the nanoscale.

Raman scattering refers to an inelastic scattering of light by elementary excitations of matter. When a photon interacts with a medium, it can be scattered in one of the three ways: a) it can be elastically scattered and thus retain its incident energy, e.g., Rayleigh scattering, b) it can be inelastically scattered by quasi-particle excitations of the medium, thereby either giving energy to the medium, e.g., Stokes scattering, or, c) removing energy from it, e.g., anti-Stokes scattering. Thus, Raman scattering involves a coupling between incident photons and the quasi-particle excitations such as phonons (lattice vibrations), magnons and electronic single particle or collective excitations within a sample, which results in the emission of light from the sample that is shifted in frequency from the incident "excitation" light. Raman scattering is an inherently weak nonlinear process that is orders of magnitude less efficient that fluorescence detection. Only when particles such as molecules are bound to metallic nanoparticle surfaces, is the efficiency increased sufficiently to be able to observe surface-enhanced Raman scattering (SERS) from single particles. See e.g., K. Kneipp, et al., *Phys. Rev. Lett.* 84: 3470-3473, 2000.)

An optical waveguide and a measurement system are provided for fluorescence detection in two-dimensional interconnected solid and liquid-core ARROW waveguides. Single molecule sensitivity and electrical control of analyte flow through the liquid core ARROW waveguides was demonstrated for deterministic generation of optical signals, such as fluorescent signals, with ultra-high sensitivity.

It has been demonstrated that integrated liquid core ARROW waveguides with fully planar beam paths are very desirable for single molecule detection due to their high efficiency, sensitivity, and inherent advantages of integrated optics. Yin, et al., *Applied Physics Letters,* 87: 211111, 2005; Yin, et al., *Applied Physics Letters,* 85: 3477, 2004. Electrical control of analyte movement in fluidic channels by methods such as capillary electrophoresis allows for faster and higher-resolution analyte separation than slab gel electrophoresis. Woolley et al., *Proc. Natl. Acad. Sci. USA,* 91: 11348-11352, 1994. Moreover, when combined with laser-induced fluorescence techniques, minute amounts of fluorescently labeled analytes, for example, nucleic acids A or amino acids, can be detected with high efficiency and precision. Schwartz et al, *Anal. Chem.* 64: 1737-1740, 1992; Sromovasan, et al., *Journal of Chromatography A,* 652: 83-91, 1993. Therefore, further integration of components for electrical control with liquid-core ARROWs will make these devices very attractive for molecular level separation of many biomolecules such as nucleic acids, DNA, RNA, protein, amino acids and PCR products in a fully planar approach.

Sensitivity limits and electrical control in integrated ARROW waveguides are discussed, in which ARROWs with liquid and solid core are interconnected with each other at 90 degrees. In order to determine the sensitivity limit of the intersection ARROW waveguides, we performed concentration-dependent fluorescence measurements on waveguides with open liquid cores as shown in the SEM image in FIG. 1a. As illustrated, fluorescence of Alexa 647 dye molecules in the mode excitation volume at the intersection (~100 fl) is excited by a HeNe laser coupled into the solid-core waveguide, and detected by avalanche photodiode in single photon counting mode (SPCM, Perkin Elmer) at the output of the liquid core. FIG. 1b shows the average detected photon counts per second as a function of the average number of molecules inside the mode excitation volume. The symbols show different experimental runs and the error bars reflect the estimated variation due to sample alignment. It can be seen that within the measurement uncertainty, we are capable of distinguishing between zero and one molecule within the excitation volume, demonstrating single molecule detection in integrated, planar ARROW waveguides.

Figure 2:
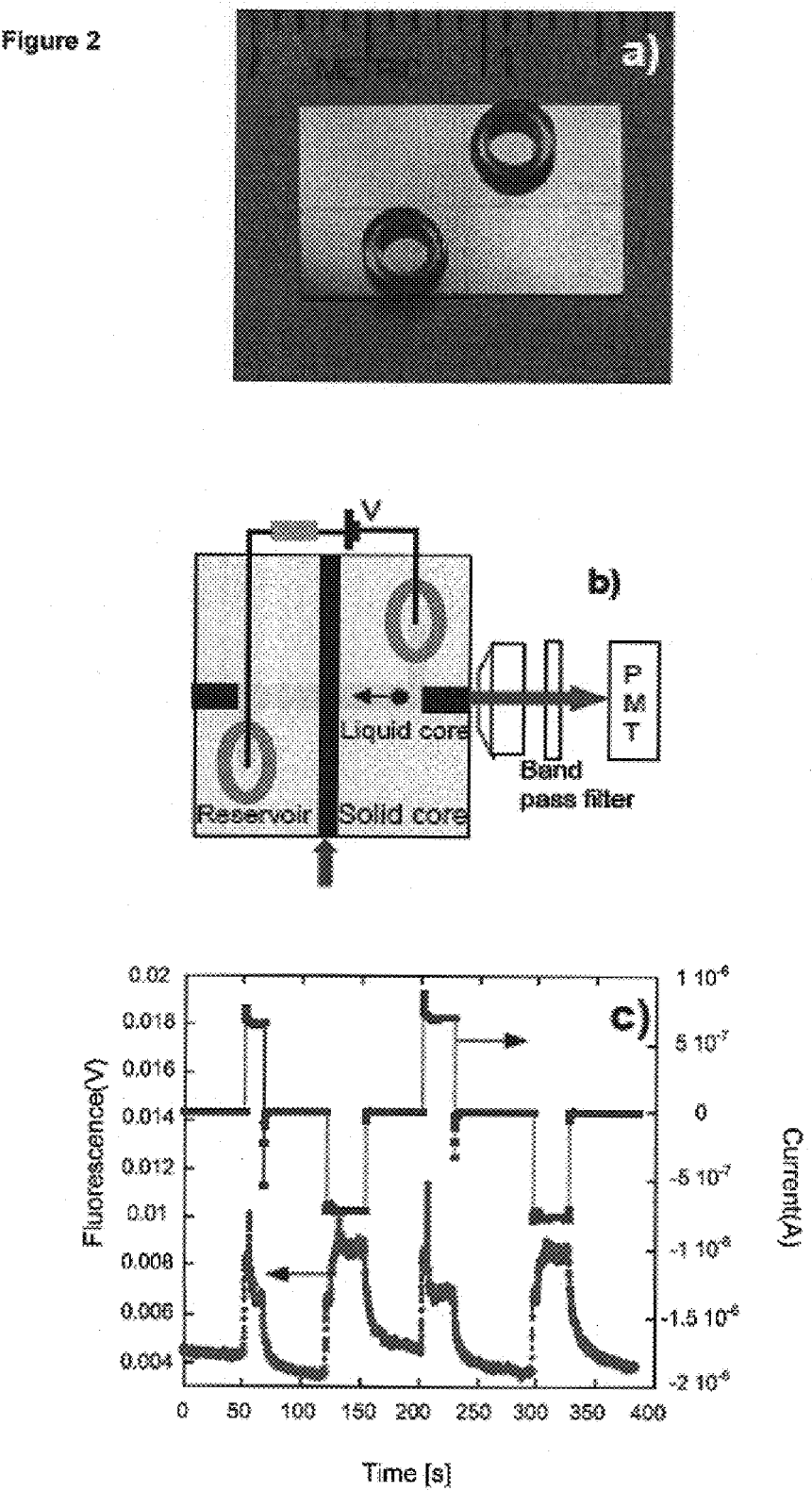
FIG. 2(a) Image of integrated waveguide sensor. (b) Schematic experiment setup of electro fluorescence detection; (c) Time trace of both detected fluorescence amplitude and the current across the liquid channel.
Figure 3A:
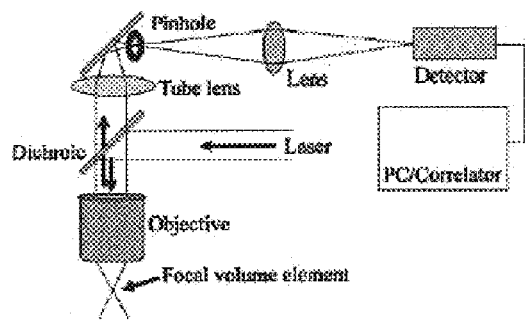
FIG. 3(a) schematically depicts a fluorescence correlation spectroscopy setup in which the sample is placed in the focal volume element.
Figure 3B:
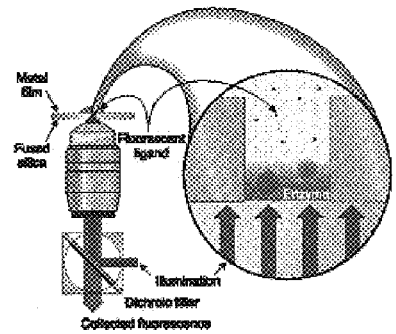
FIG. 3(b) depicts an apparatus for single-molecule enzymology. In both setups, fluorescence is excited and detected perpendicular to the wafer plane, and bulk optics are used.
Figure 4A:
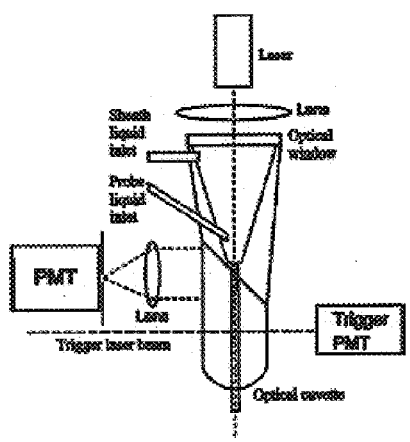
FIGS. 4(a) and 4(b) illustrate flow cytometry setups. In both cases, light cannot be guided along the liquid channel and is detected in the perpendicular direction.
Figure 4B:
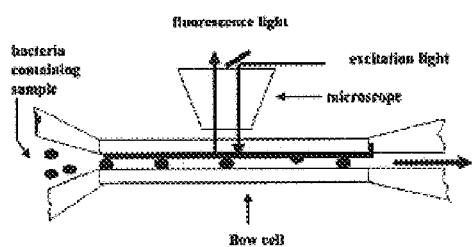
Figure 5A:
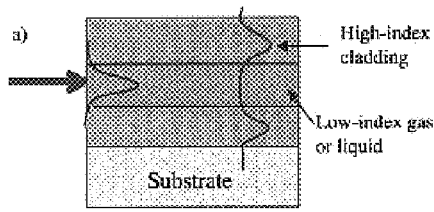
FIG. 5(a) illustrates a conventional microchannel in which low-index materials are surrounded by high-index cladding material, and where light is not guided and leaks into the claddings quickly.
Figure 5B:
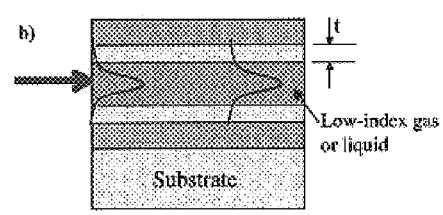
FIG. 5(b) depicts an ARROW waveguide structure in which high-index cladding layers of correct thickness keep light inside the core and enable guiding.

To add electrical control of the sample molecules to the waveguides described above, two reservoirs were glued right on top of the two ends of S-shape liquid cores on the surface of the chip, and the two optical outputs of the liquid core were sealed by two solid core waveguides with aligned cores (FIG. 2a). FIG. 2b shows the schematic experiment setup. The liquid core channels were first filled by pipeting buffer solution (0.01 M KCl) into the reservoirs. Then, two platinum electrodes were placed in the two reservoirs, respectively, to apply a voltage across the whole channel. At the same time, the optical path was aligned so that the fluorescence output can be collected by a microscope objective lens and focused onto a PMT detector. A fluorescence band pass filter was placed in front of the detector to eliminate the pumping light. About 1 mW pumping power of He—Ne laser was coupled from singlemode fiber into the solid core pump channel and guided to the intersection. After that, anionic fluorescent dye molecules (Alexa 647) were pipeted into the cathode reservoir. An applied voltage moves the molecules from cathode to anode as shown. Due to the interconnection waveguide geometry of the sample, fluorescence is generated only when the molecules pass through the intersection. Thus, separation of different molecules can be achieved by recording the fluorescence amplitude as a function of time. The blue arrow represents the pump beam path, and the red arrow represents the fluorescence signal. FIG. 2c shows the time trace of both detected fluorescence signal and the current of the electrical control circuit as drawn in FIG. 2b. The trace clearly shows that the dye molecules were driven back and forth through the intersection by switching the polarity of the two electrodes in the reservoirs as the fluorescence amplitude goes up and down. The applied voltage is 200V and the velocity of the molecules was 0.28 mm/s. The value was deduced from the time gap between the rising edge of the current and the rising edge of the fluorescence amplitude.

Single molecule sensitivity and electrical control of fluorescence detection has been demonstrated in an integrated semiconductor chip based on integrated intersection ARROW waveguides with fully planar beam geometry.

An apparatus is provided for simultaneous optical and electrical sensing with single-molecule sensitivity based on integration of biological and synthetic nanopores or micropores with optical waveguides. The nanopore acts "a smart gate" for controlling the number and position of molecules in numerous parallel waveguide channels on a single chip. Such an integrated device has applications in genomics, proteomics, disease detection, homeland security, toxicology, gas and liquid sensing. Integrated nanopore waveguide devices not only afford single molecule resolution for electrical and optical measurements independently, they also enable novel approaches that are based on this unique combination of both concepts.

This approach compared to other state-of-the-art techniques further provides:

Integration of biological or synthetic nanopore or micropore with integrated optical waveguides: provide controlled entry of individual entities, for example, molecules, proteins, viruses, or cells, into an integrated optical waveguide sensor through a nanoscopic opening in the channel. The entry itself produces an electrical signal with single-molecule sensitivity.

Spatio-temporal synchronization of optical and electrical sensing capability allow individual entities to be probed and measured at different times within the waveguide.

Parallel nanopore or micropore/ARROW sensors on a chip with single optical pump path allow the use of a single optical signal to excite multiple channels.

Simultaneous recording of electrical current blockade signals and optical fluorescence or Raman scattering signals can occur with single-molecule sensitivity.

The approach provides a novel scheme for DNA sequencing using optical fluorescence and nanopore or micropore gate.

The approach provides a novel scheme for DNA sequencing using surface-enhanced Raman scattering and nanopore or micropore gate.

The approach provides a novel scheme for cell flow cytometry on a chip.

The integration of nanopores with the ARROW waveguides will enable controlled insertion and translocation of single molecules through synthetic nanopores into the waveguide channel. Because both ARROW and nanopore technologies rely on the same material (silicon nitride), their integration has a natural affinity. In addition, the diameters of biomolecules, such as a prokaryotic ribosomes (20 nm for E. coli), are a perfect match for the capabilities of synthetic pore fabrication technology. Integration will address the opening of a nanopore on the ARROW waveguide, provision of suitable fluidic connections for introduction and extraction of biological material in solution, and placement of electrical connections to promote the directional movement of the sample molecules through the waveguide core.

Implementation of a fully integrated sensor is shown in FIG. 34. Such a sensor will provide electrical (e.g., hairpin-DNA formation energy) and optical (e.g., conformational dynamics) sensing capabilities, and enable additional functionality via simultaneous use of electrical and optical signals. Liquid-core ARROW waveguides are integrated on a silicon chip for single molecule fluorescence sensing. Excitation (blue) and fluorescence (red) paths run in the sample plane and are accessible with fiber optics. Fluid reservoirs and electrical contacts are integrated on the chip as shown. A nanopore is placed at one end of the hollow core and fulfills a dual purpose. First, it produces current blockade signatures for analysis of biomolecule translocation through the pore. Secondly, it acts as a controllable gate for introduction of individual molecules into the optical sample volume enabling single molecule fluorescence at the waveguide junction.

Many waveguide channels can be integrated on one wafer to build highly parallel two-dimensional optical and electrical sensor arrays.

Finally, integration of fluidic reservoirs is required for controlled introduction of biomolecules in the liquid-core waveguide. We have demonstrated that poly-methyl-methacrylate (PMMA) reservoirs can be attached to these samples and demonstrated electrophoretic separation of amino acids inside hollow-core channels similar to ARROWs but without optical confinement. This demonstrates that biomolecules can indeed be moved through our structures using applied electric fields. The fluidic reservoirs and their placement on top of the envisioned waveguide geometry is shown in FIG. 31a and 31b.

Figure 30:
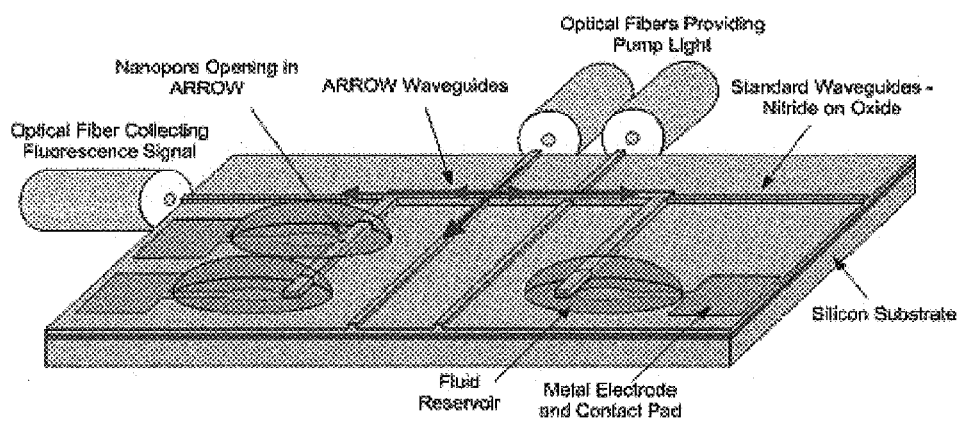
FIG. 30 illustrates an envisioned integrated nanopore waveguide sensor for single molecule studies.

In particular, FIG. 31b is a photograph of a chip that has just been completed and contains all essential elements of the envisioned sensor as shown in FIG. 30. It shows an S-shaped liquid-core waveguide running horizontally. Its ends are covered by two PMMA cylinders that will be used to supply liquid sample material to the hollow core. Two solid-core pump waveguide run from top to bottom and intersect the center of the liquid-core waveguide. Light generated in the liquid core will be coupled into solid-core waveguides that carry the signal to the left and right ends of the chip (see also FIG. 30). This demonstrates our capability to fabricate the envisioned integrated sensor chip. Optical testing on this chip will be done in the near future.

The present invention demonstrates that ARROW waveguides can be used to guide light through small volumes of liquid solution on a chip, that biological and synthetic nanopores can provide single molecule resolution through electrical measurements, for example, in the study of biomolecules such as ribosomes. The translation mechanism in ribosomes is an area for research in molecular biology that can benefit from optical studies on the single molecule level. A further example of implementation of the present invention is nucleic acid sequencing of a single DNA molecule, as shown in FIG. 28. The present invention combines these areas into a coherent program on optical and electrical sensing of single biomolecules on a chip.

One goal of ours is to have highly functional, highly parallel structures naturally combined with other integrated elements such as interferometers and detectors on the same chip. The research described herein provides the first crucial steps in this direction: the demonstration of waveguiding in ARROW structures with liquid core layers and the fabrication of simple elements suitable for fluorescence measurements on DNA molecules. We point out that the ARROW principle is well understood and being used in other areas. This will also be the first planar setup relying entirely on techniques successfully used in integrated optics.

As a result of our research, better measurement tools will evolve that will improve both our fundamental understanding of health-related processes in cells and molecules as well as lead to improved flow cytometry methods.

Below we provide a more detailed description of exemplary embodiments and applications of the present invention. The bulk focuses on fluid applications, however, these parts are also applicable to gases. In addition, it should be noted that invention may be carried out with a variety of substrate and waveguide materials, including the materials discussed in connection with the examples described below as well as those listed below (this list is not intended to be exhaustive):

Exemplary substrates:
Semiconductors (useful for integrating electronic and optoelectronic devices (III-V semiconductors) with the waveguide), including silicon, Ge, all III-V semiconductors(GaAs, InP, HgCdTe, GaN, GaP, etc.).
Metals (useful for making a low cost device), including Al, Tin, Titanium, Copper, etc.
Plastics and Polymers (again useful for a low cost device and integrating with electronics on PCB boards). Insulators like ceramic or glass (useful because they produce a transparent substrate or because of heat mitigation).
Silicon based glasses—silica, quartz, soda lime, boron doped, etc.
alumina, sapphire, diamond Exemplary waveguide materials:
Any material possibly deposited by chemical vapor deposition, including silicon dioxide, silicon nitride, silicon oxy-nitride (important because they are very commonly deposited by chemical vapor deposition).
Any material that could be sputtered or evaporated onto a substrate, including silicon dioxide, silicon nitride, and silicon-oxynitride.
Any material that could be spun-on or dip coated including spin-on-glass, polyimides, and polymer based materials.

Exemplary sacrificial layer materials:
Any metal, including aluminum, silver, gold, titanium, tungsten, copper.
Polymer materials, including SU8, photoresist, and polyimide.
Any material that can be chemically etched without affecting the overcoating waveguide materials Exemplary nanopore materials:
Silicon membrane
Silicon nitride membrane
Silicon dioxide membrane
$\alpha$-hemolysin pore in a lipid membrane Detailed Description of Exemplary Implementations and Applications We will now explain our invention in sufficient detail to enable a person of ordinary skill in the field of integrated optics to make and use the invention without undue experimentation. The following description is not intended (nor would it be possible) to serve as an exhaustive discussion of every possible embodiment, application or method of manufacturing a device within the scope of our invention. It is sufficient, however, to enable the skilled artisan to practice our invention. We will first briefly discuss our preliminary studies and then we will explain a method for fabricating exemplary embodiments of the invention, optical measurements for characterization and testing, a phase-shift device based on electromagnetically induced transparency, and a possible implementation of an integrated "optical tweezers" in accordance with the present invention. Other possible implementations include nucleotide sequencing of a single DNA molecule or a single RNA molecules, measurement of cell flow cytometry of a single cell or of a single ribosome.

Preliminary Studies

To date, we have fabricated and tested hollow-core ARROW waveguides with both gaseous and liquid cores and demonstrated low-loss propagation through both types.

1. Waveguides with Air Cores

For the design of the hollow-core ARROW waveguides, we chose cladding materials that are compatible with silicon microfabrication and offer the best potential for further integration. Hence, the transverse profile of the waveguide consists of alternating layers of silicon nitride and oxide (n=2.1 and 1.46, respectively, see FIG. 8(b)). The required thicknesses $d_i$ for the i-th cladding layer of the required Fabry- Perot reflector at our design wavelength of 785 nm can be determined in the same way as for an all-solid ARROW waveguide and are given by $$d_i = \frac{\lambda}{4n_i}(2N+1)\left[1 - \frac{n_c^2}{n_i^2} + \frac{\lambda^2}{4n_i^2 d_c^2}\right]^{-0.5} \quad (1)$$

where $n_i$ and $n_c$ are the cladding and core refractive indexes, respectively. For $n_c=1$ (air), this results in layers of 109 nm (SiN) and 184 nm (SiO$_2$) in the lowest order (N=0). One advantage of the ARROW approach is that the layers do not have to be periodic. As long as the correct $d_i$ for a given material is chosen that layer will reduce the propagation loss. FIG. 8(c) shows the calculated transverse power propagation loss as a function of core thickness $d_c$ for different structures. The black line represents the loss without ARROW confinement, i.e., an air core surrounded by a silicon nitride layer, and shows that propagation in cores with diameters less than 20-30 μm is not feasible. FIG. 8(c) shows the loss for the case where the ARROW cladding consists of one silicon nitride and one air layer on each side of the core, which reduces the loss drastically. However, incorporating two more air layers poses severe fabrication problems. FIG. 8(c) also shows the loss if periods of alternating oxide and nitride layers are used. Each additional period reduces the loss by a factor of approximately 3. Clearly, a tradeoff exists between reduction in waveguide loss and fabrication complexity. We chose to fabricate structures with three top and bottom periods which result in a transverse mode loss of 1.1 cm$^{-1}$ for $d_c=3.5$ μm (dash-dotted line).

The second important design consideration is the realization of lateral confinement for effective single mode propagation. We analyzed different types of lateral confinement. FIG. 8(d) shows a rectangular core with uniform cladding layers where all confinement is realized using the ARROW principle. FIG. 8(e) shows a similar structure that includes an optimized etch of the top SiO$_2$ layer to enable effective index confinement in the lateral direction. In this case the mode would be confined to a narrower area underneath the ridge and somewhat lower propagation loss is possible. However, 2D loss simulations show that the etch depth has to be controlled very carefully (within a few nm), which poses additional fabrication challenges.

After determining the structure for lowest loss, two major issues were addressed in order to fabricate the waveguides: The first was finding a suitable sacrificial core layer with lateral dimensions on the order of microns and lengths up to several centimeters. The second issue was growing sufficiently thick top layers over the hollow core to provide mechanical stability.

FIG. 8(f) shows an SEM micrograph of a completed hollow-core ARROW waveguide using the following process steps, which are represented generally by FIGS. 9(a)-9(d):

1) Alternating oxide and nitride layers were deposited on a silicon substrate using plasma-enhanced vapor deposition (PECVD) to form the bottom cladding layers. Deposition was carried out at temperatures between 250° C. and 300° C. Deposition rates for nitride and oxide layers were 70 Å/min and 200 Å/min, respectively. See FIG. 9(a).

2) Subsequently, a 3.5 μm thick photosensitive polyimide (SU-8) layer was deposited on the substrate and then patterned into 2 cm-long ridges of varying width (6-50 μm). See FIG. 9(b).

3) The top ARROW layers and a 2.944 μm SiO$_2$ cap layer for mechanical stability were grown. The thickness of the top layer was chosen such that it provides additional confinement according to eqn. (1). See FIG. 9(c).

4) To create the hollow waveguide cores, the sacrificial SU-8 layer was removed using a solution of H$_2$O$_2$ and H$_2$SO$_4$ at 85° C. providing the required high directional etch selectivity. A photoresist ridge was then patterned on top of the waveguide and transferred into the top SiO$_2$ layer using CF4 based plasma etching. (It should be noted that one can do this processing using different materials as sacrificial layers, such as metals (aluminum), polyimides (SU-8), and photoresist.) This ridge was added to evaluate the possibility for lateral confinement. As can be seen from FIG. 9(d), almost perfectly rectangular cores with excellent smoothness can be fabricated using this method.

The completed samples were cleaved into 0.5-8 mm long waveguides and light from a diode laser at 785 nm with 0.25 mW power was coupled into the structures. The near-field image of the mode profile at the output facet was recorded using magnifying optics (0.85 NA lens, 60:1 magnification) and a CCD camera (BeamPro Model 2320, Photon Inc.) while simultaneously illuminating the output facet to image both facet and ARROW mode directly. For the first time, low loss propagation through an integrated ARROW waveguide with a hollow air core was observed. The mode image is shown in FIG. 8(g) for a waveguide with 12 μm core width, 3.5 μm core height, and 2 mm length (same dimensions as FIG. 8(f)). The black lines outline the facet of the waveguide since the microscope image is not as clear as the SEM micrograph. The optical mode (bright ellipse) is clearly confined inside the hollow air core. In FIG. 8(h) the intensity profile of the ARROW core mode is shown. A single mode (fundamental ARROW mode) is observed. The intensity FWHMs of the mode are 1.32 μm (transverse direction) and 6.4 μm (lateral), respectively. This corresponds to a mode area of 6.641 μm$^2$. To our knowledge, this is the smallest optical mode observed in air to date.

FIGS. 8(i) and 6(j) show the transverse and lateral cross sections through the center of the waveguide (circles) in comparison with the theoretically expected profile (solid line) of the fundamental ARROW mode according to our design specifications. For the lateral mode calculation the structure was assumed to have no etched ridge in the top SiO$_2$ layer. No fitting parameters were used and the agreement between theory and experiment is excellent. FIG. 8(g) also demonstrates that the lateral confinement results from the vertical ARROW layers rather than the ridge in the top SiO$_2$ layer as effective index guiding would have led to a narrower mode.

The waveguide loss of the ARROW structure was determined by recording the transmitted power as a function of waveguide length (input polarization along y). The result is shown in FIG. 8(k) for a waveguide with a lateral width of 24 μm. By fitting the data to an exponentially decaying line, a waveguide loss of 6.5 cm$^{-1}$ was deduced. For comparison of this value to theoretical expectations, coupling of several modes into the core was taken into account. Since the fiber is aligned to the waveguide center, the light is coupled predominantly into odd ARROW modes. The coupling coefficients $\beta_i$ and loss values $\alpha_i$ (calculated with commercial 3D mode solver FIMMWAVE) for the first, third and fifth mode are 28.6%, 15.3%, 12.6% and 3.29 cm$^{-1}$, 21.79 cm$^{-1}$, and 64.37 cm$^{-1}$, respectively. The expected output intensity is $$I_{out} \propto \beta_1 e^{-\alpha_1 L} + \beta_3 e^{-\alpha_3 L} + \beta_5 e^{-\alpha_5 L}$$

and the resulting curve is shown in FIG. 8(*k*) as dashed line with an average loss of 3.7 cm$^{-1}$. The remaining discrepancy between theory and experiment is due to scattering losses and thickness fluctuations of the ARROW confinement layers, especially in lateral direction. The magnitude of the loss is mainly given by loss in lateral (y) direction. There are several ways to reduce the loss significantly in the future. These include lateral variations of the core thickness as has been used for large area hollow waveguides with metal claddings, additional ARROW layers, or the use of semicircular, curved, or arched core shapes which can be achieved using a modified sacrificial layer process.

2. Liquid Cores

Here, we designed a waveguide with layers of 110 nm (SiN) and 281 nm (SiO2) for low loss propagation in water (n=1.33) at 690 nm. This optimizes the structure for fluorescence emission of dye molecules that are excited by a He—Ne laser at 635 nm. The waveguides were fabricated in the same way as for air cores.

For optical characterization, the samples were cleaved into waveguides with variable length (0.5 to 8 mm) and light from a He-NE laser at 635 nm or a diode laser at 785 with up to 1 mW power was coupled into the waveguide cores using single-mode fiber. For measurements with liquid cores, the cores were filled with ethylene glycol and then mounted on a translation stage for transmission measurements. Ethylene glycol (n=1.43) was used instead of water because it evaporates more slowly and allows for longer measurement times.

The near-field image of the mode profile at the output facet was recorded in the same way as for the air core sample and led to the same results, i.e., observation of a confined and propagating mode inside the non-solid ARROW waveguide core.

The waveguide loss was determined by measuring the intensity throughput as a function of waveguide length. By fitting the data to a decaying exponential, a loss of 2.4 cm$^{-1}$, is observed at 635 nm for a sample with core width 24 μm. At 785 nm, we could not observe any transmission, which implies a loss of at least 10 cm$^{-1}$ based on the current sensitivity of our setup. The experimental values are in qualitative agreement with the expectation of higher loss at longer wavelengths and the discrepancy is mainly due to contributions from coupling into higher order ARROW modes with significantly higher loss and scattering losses in the waveguide. We emphasize that the wavelength dependence of the loss is strong and can effectively be used to suppress propagation at certain wavelengths. In addition, this dependence can be tailored by choosing the ARROW layer thicknesses while maintaining low loss at one design wavelength. This wavelength selectivity makes these waveguides especially attractive for fluorescence and Raman scattering applications where filtering of a pump beam from a signal at longer wavelengths is required. Together with the high coupling efficiency of fluorescence into the ARROW mode, this feature makes liquid core ARROW waveguides ideally suited for optical measurements with single molecule resolution.

Based on the preliminary results on single waveguides described above, ARROW waveguides with non-solid cores can be used for highly parallel sensor architectures with multiple ARROW sensor waveguides on the same chip. A possible implementation of such a device is shown in FIG. 13. In this top view, three ARROW channels are shown into which sample fluids can be injected using microfluidic connections. One implementation would use PDMS structures over a liquid reservoir that is connected to the actual optical waveguide. Liquids are injected into these reservoirs using syringes. The ARROW waveguides can be intersected by conventional optical waveguides to couple excitation light for fluorescence or Raman scattering into the sample channel. The advantage of this technology is that several pump waveguides can cross a single ARROW channel and that a single pump waveguide can intersect multiple ARROW channels to excite fluorescence in more than one sample volume. This leads to highly connected, parallel sensor architectures. The pump waveguides are realized in SiO2 using conventional index waveguiding for lateral confinement and ARROW waveguiding for transverse confinement. In another implementation, the excitation could occur via the ARROW waveguides and collection through the conventional waveguides.

Other Approaches to Quantum Optics on a Chip

Very recently, researchers have started to develop experimental platforms to perform quantum optical experiments on the surface of a chip using mechanisms to trap, manipulate, and move atoms. Bartenstein, M. et al., *IEEE Journal of Quantum Electronics* 36, 1364, 2000; Hansel, W. et al., *Nature* 413, 498, 2001. In addition, the use of quantum coherence for the realization of atomic clocks has been proposed. Kitching, J. et al., *Appl. Phys. Lett.* 81, 553, 2002. This shows that the knowledge acquired from integrating EIT with a semiconductor chip will influence non-EIT-based research and science as well.

Proposed Approaches

The discussion above has made it clear that ideally we would like to have an EIT medium with the optical qualities of alkali vapor atoms and the practical advantages of a semiconductor. Since no single medium seems to exist that inherently combines both features, we propose a way to actually use alkali atoms, but integrate them on a semiconductor chip as a host medium. The advantages inherent to such an approach are:

maximum interference: By creating atomic vapor-containing cavities on a chip whose properties are comparable to bulk cells, interference effects can be realized with maximum strength.

compact size: Most, if not all of the bulk optics are unnecessary. All that is required is to couple light into the waveguide, which can be done with standard fiber optics methods. The length of the Rb-cavity can easily be varied between nanometers and millimeters.

simplicity: The amount of required alignment is significantly reduced, making such an EIT-chip much more robust to environmental impact. For example, beam splitters can be realized with 3 dB waveguide couplers, standard waveguiding methods ensure automatic alignment of the beams with the Rb cavity, etc. If source and detector are integrated on the chip, there is absolutely no alignment necessary.

versatility: The large available suite of microprocessing techniques opens the possibility to add more complex controls to an EIT structure. For example, electrical contacts can be lithographically defined to apply electric fields or pass current to generate precise magnetic fields at the cavity location. Other examples include straight-forward and accurate temperature control.

scalability: Once the fabrication method has been developed for one cavity, it is easily possible to define multiple cavities on the same chip, which could serve different purposes.

A comprehensive program to realize such integrated structures needs to address several areas: These are sample design and simulations, development of suitable fabrication methods, building a spectroscopy setup, and testing of structures and devices. The following approaches to address these issues are described.

Materials and Waveguide Design

One of the main new contributions of this work is the insertion of a low index (essentially air) gap into a (ideally single-mode) waveguide structure. A main consideration is to choose a suitable material system in which to realize the waveguides. The material system needs to have the following properties:

- guiding of light at the atomic transmission wavelength (e.g., 795 nm for the D-line in Rb)
- allow for design of single-mode waveguide structures
- allow for etching cavities for integrated Rb-cell
- allow for integration with other optoelectronic and photonic elements Antiresonant Waveguide (ARROW) Structures on Silicon Non-solid core ARROW waveguides are ideally suited for realizing longer cavities in combination with single-mode waveguides. As described above, if the layer thicknesses are chosen such that the thickness of a low-index core and a high-index cladding are $m\lambda/2$ and $(2m+1)\lambda/4$, respectively, light propagation occurs in the low-index layer and the structure forms a so-called antiresonant reflecting optical waveguide (ARROW). Duguay, M. A. et al., *Appl. Phys. Lett.* 49, 13, 1986; Koch, T. L. et al., *Elec. Lett.* 23, 244, 1987.

This concept can be used to our advantage by fabricating an ARROW structure where air is the low-index core in which light propagation occurs. Since the index of the Rb cavity is similar, the wave will remain confined in this region and diffraction and coupling losses are significantly reduced. A thin transmissive wall of silicon would separate the air core from the Rb cell. While MEMS-based methods can be used to realize ARROW structures for integrated optics (Nathan, A. et al., *Proc. SPIE* 2686, 2, 1996) and ARROW structures can be integrated with photodetectors on the same chip (Benaissa, K. et al., *J. of Lightwave Technology* 16, 1423, 1998), the fabrication of such a structure is more challenging than the simpler slab waveguides.

ARROWs or ARROW waveguides also encompasses other dielectric confinement methods where the layers are periodic, such as Bragg mirrors, one-dimensional photonic crystals and omniguides.

Optical Tweezers

Optical tweezers provide a method to hold, direct and manipulate small particles of micron or sub-micron size such as cells or cell parts using light (Ashkin A. *IEEE Journal of Selected Topics in Quantum Electronics*, 6, 841-56, 2000 and references therein). This has the advantage that no mechanical interaction is present that could damage the specimen. The effect is based on light pressure, i.e., the notion that light carries with it a certain amount of momentum that can be transferred to material objects.

An optical tweezer is generally understood as being a single-beam optical trap as shown in FIG. 14($a$) where a laser beam is strongly focused by a high aperture lens. Two types of forces result as the beam hits a small object. One is a scattering force that pushes the object along the direction of the beam, i.e., along x. The second one is the trapping force F, which is directed along −x. If the aperture of the lens is large enough, the trapping force can dominate over the scattering force and trap a particle at a point close to the focus of the lens. No integrated version of such tweezers exists to date. By deliberately shaping (tapering) the lateral profile of an integrated ARROW waveguide with non-solid core (central tapered area in FIG. 14($b$), the intensity profile of a Gaussian beam can be emulated. In the same way as in traditional optical tweezers using lenses, the intensity gradient of light propagating along x will induce scattering and trapping forces on a microscopic particle inside the waveguide, leading to an integrated version of optical tweezers. Note that no lenses are required in this case and that the beam profile can be shaped and designed in ways different from profiles obtainable from bulk optics. In a particular application, this concept can be used to hold a particle at the intersection of the ARROW waveguide with another waveguide as shown in FIG. 14($b$). This can facilitate optical experiments such as fluorescence studies on the sample particles.

Fluorescence Measurements

After characterizing various structural and optical properties of the waveguides, we carried out fluorescence studies on conventional organic dye molecules (Alexa 647, © Molecular Probes, in glycol) and clearly demonstrated the applicability of the ARROW concept to molecular sensing.

Figure 15:
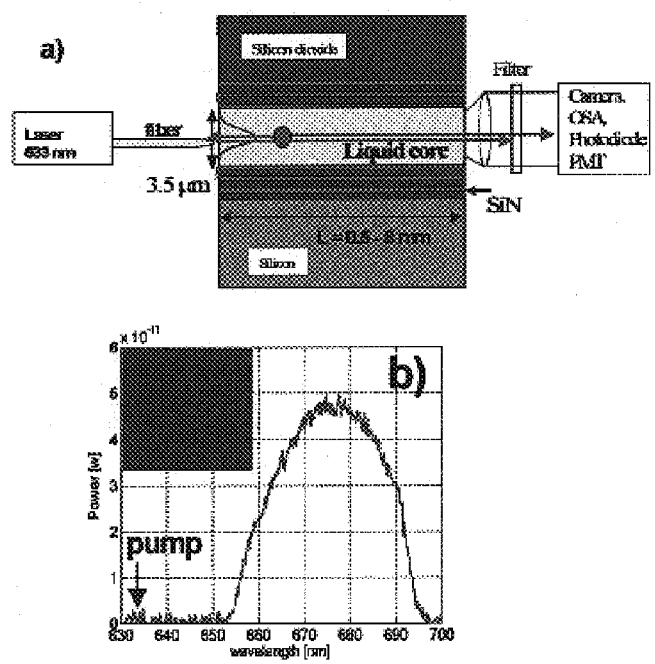
FIGS. 15(a) and 15(b) illustrate a) Fluorescence setup. b) Fluorescence spectrum. Inset: Fluorescence emitted at end facet of ARROW waveguide.
Figure 16:
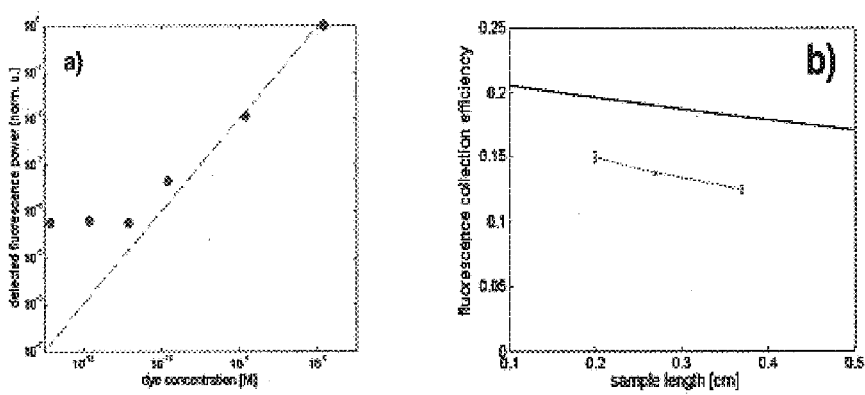
FIGS. 16(a) and 16(b) illustrate a) Fluorescence power vs. dye concentration (circles: experiment, line: linear fit). b) Fluorescence collection efficiency (line: theory, dotted line: experimental results with error bars.)

FIG. 15 illustrates a) Fluorescence setup. b) Fluorescence spectrum. Inset: Fluorescence emitted at end facet of ARROW waveguide. FIG. 15$a$) shows an experimental setup. Light from a laser diode or He—Ne laser at 633 nm is fiber-coupled into the ARROW waveguide where it excites dye molecules in solution. The emitted fluorescence is captured with a high-NA lens, filtered, and recorded with a CCD camera, spectrum analyzer, or photomultiplier tube (Hamamatsu). FIG. 15$b$) shows the observed fluorescence spectrum with clear suppression of the 633 nm pump. The inset shows the image of light emitted from the end facet of the waveguide. These experiments were carried out with varying concentration of dye in a 1.8 mm long waveguide. FIG. 16 illustrates a) fluorescence power vs. dye concentration (circles: experiment, line: linear fit). b) Fluorescence collection efficiency (line: theory, dotted line: experimental results with error bars.) Fluorescence was detected down to a concentration of 10 picomoles/l, or less than 500 molecules in the waveguide (FIG. 16$a$). Lower concentrations could not be resolved due to the sensitivity limit of the PMT and background fluorescence from the solvent (75 picoliters). The measured collection efficiency of the fluorescence was as high as 15% per facet in good agreement with theory (FIG. 16$b$). D. Yin et al., "Highly efficient fluorescence detection in picoliter volume liquid-core waveguides," *Appl. Phys. Lett.*, 87: 211111, 2005. The collection efficiency drops for longer sample length due to the intrinsic waveguide loss.

Figure 17:
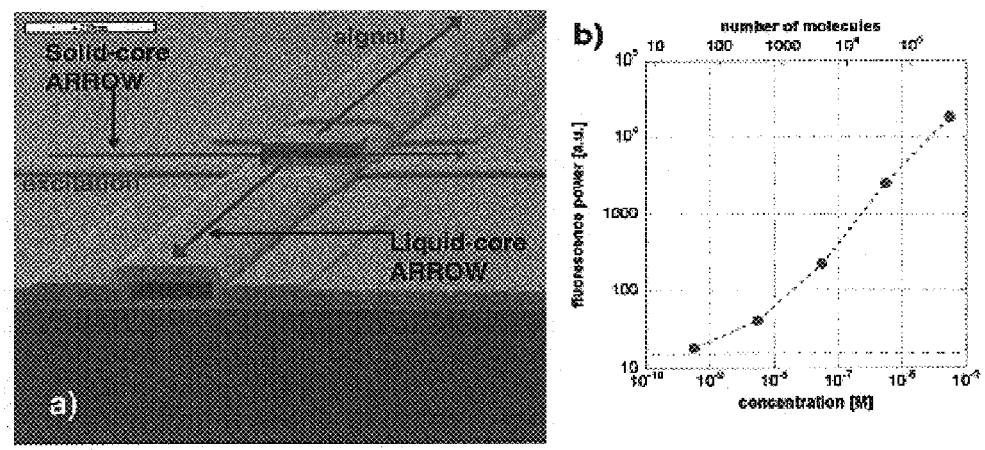
FIGS. 17(a) and 17(b) illustrate a) Beam paths and excitation volume in intersecting waveguides, b) fluorescence power versus dye concentration (dashed line: detector background).

Recently, we demonstrated fluorescence detection from intersecting waveguides, i.e., in the desired geometry for the sensor application. FIG. 17 illustrates a) beam paths and excitation volume in intersecting waveguides, b) fluorescence power versus dye concentration (dashed line: detector background). FIG. 17$a$) shows again the intersection region along with the excitation and collection geometry. Other parts of the experiment (laser source, powers, detector) are the same as above.

Figure 18:
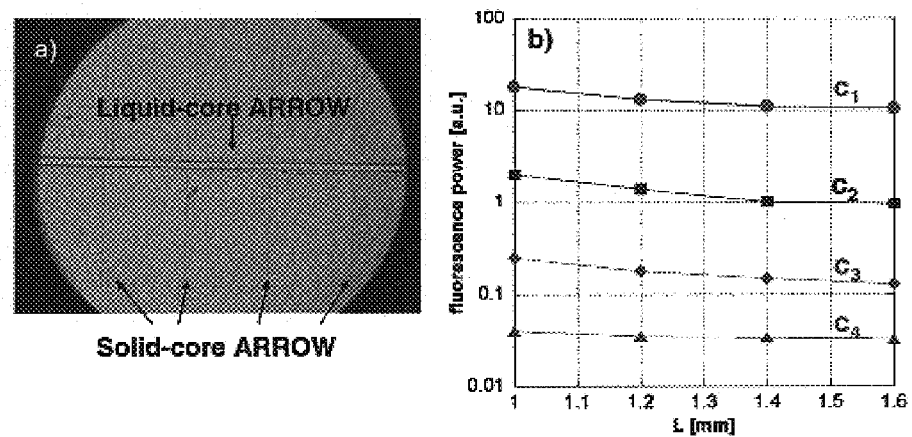
FIGS. 18(a) and 18(b) illustrate a) Microscope image of waveguide intersections, b) fluorescence power versus excitation position for four dye concentrations ($c_1$-$c_4$).

Finally, we observed fluorescence excitation at multiple locations along the liquid channels which demonstrates that highly parallel 2D waveguide arrays can be built and which will be important for our proposed FRET measurements on ribosomes (see below). FIG. 18 illustrates a) microscope image of waveguide intersections, b) fluorescence power versus excitation position for four dye concentrations ($c_1$-$c_4$). FIG. 18$a$ shows a microscope image of a liquid core intersected by four solid core pump waveguides spaced by 200 µm. FIG. 18$b$) shows the detected fluorescence as a function of pump location for four different dye concentrations. Fluorescence is detected from all four intersections with slightly decreasing efficiency for increasing distance to the waveguide output.

Nanopores or Micropores

An optical waveguide is provided comprising a substrate and multiple layers of solid state material disposed on the substrate, a non-solid core extending through at least one of the multiple layers, and a nanopore or micropore in fluid communication with the core. Current studies on single DNA molecules have used current blockade measurements in α-hemolysin pores. D. Deamer and D. Branton, *Acc. Chem. Res.*, 35, 817, 2002. In the present application, we focus on results of optical waveguides with synthetic nanopores or micropores formed in a layer of solid material, such as a dielectric or metal. The layer of solid material can be a silicon nitride membrane or a silicon membrane. The nanopore or micropore can be formed or drilled into the layer of solid material, for example, a silicon nitride membrane or a silicon membrane.

The nanopore in fluid communication with the non-solid core is configured to limit passage of a sample material through the nanopore to a single molecule at a time. A nanopore is an opening with nanoscopic dimensions, for example, a diameter of from about 1 nanometer to about 500 nanometers. Depending on the dimensions of a single molecule or ribosome, the diameter dimensions of the nanopore can be from about 1 nm to about 500 nm, from about 1 nm to about 100 nm, or from about 1 nm to about 2 nm. A micropore is an opening of microscopic dimensions, for example, the diameter can be from about 1 micron to about 500 microns. For use in cell flow cytometry, the micropore can be, for example, from about 1 μm to about 500 μm, from about 1 μm to about 100 μm, from about 1 μm to about 10 μm, or from about 1 μm to about 5 μm. The nanopore can be configured to limit passage to a single molecule or a single particle at a time. The single molecule or particle can include, but is not limited to, one double-stranded nucleic acid molecule, one single-stranded nucleic acid molecule, one polypeptide molecule or one ribosome. The micropore can be configured to limit passage to a single cell or viral particle at a time.

Figure 19:
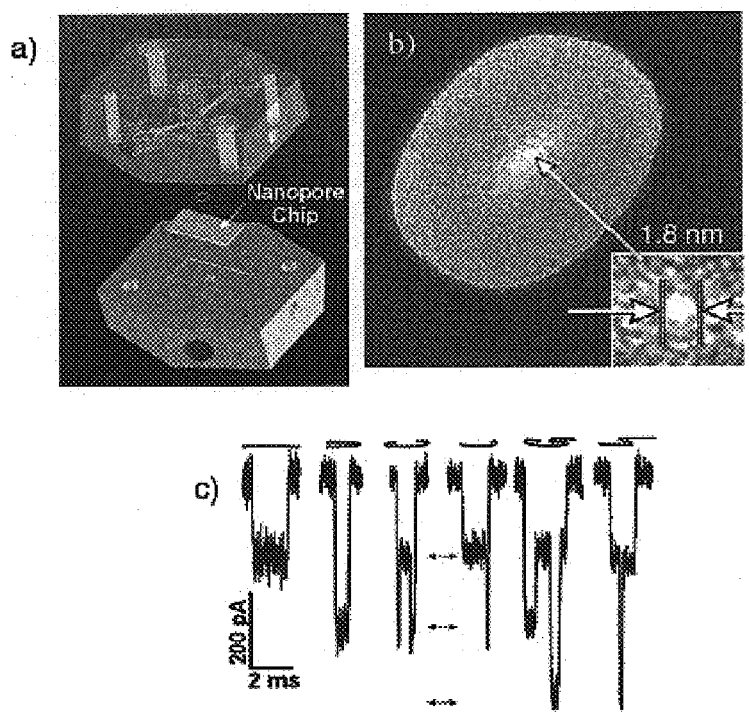
FIGS. 19(a), 19(b), and 19(c) illustrate a) Agilent-Harvard nanopore mounting device. b) nanopore in SiN after size reduction by Ar-beam reflow (after [63]), c) current blockade signal from DNA in synthetic pore obtained by Harvard group depending on DNA shape (top row).

Synthetic nanopores. Focused ion beams (FIB) are used to 'drill' a nanoscopic hole with dimensions similar to the α-hemolysin pore into a synthetic SiN membrane. The advantage of this approach is the control of size and durability of the pore as well as its compatibility with other microfabrication steps. Silicon nitride nanopores of varying size from 7 to 70 nm are provided from Agilent Technology. FIG. 19 illustrates a) Agilent-Harvard nanopore mounting device. b) nanopore in SiN after size reduction by Ar-beam reflow (after) c) current blockade signal from DNA in synthetic pore obtained by Harvard group depending on DNA shape (top row). Jiali Li et al., *Nature*, 412, 166, 2001. FIG. 19a shows a diagram of a nanopore chip placed in a microfluidic fixture for current blockade measurements. FIG. 19b shows an SEM image of a nanopore, which illustrates how the larger (dark-grey) pore is sculpted by a focused ion beam (FIB) and then reduced in size by a second exposure to a diffuse argon beam. Jiali Li et al., *Nature*, 412, 166, 2001. FIG. 19c shows current blockade signals obtained using a 10 nm synthetic pore and double-stranded DNA. The pore is capable of resolving individual molecules and of providing information about their folding state (top row).

Pores in hollow-core structures. In the context of this application, the use of SiN membranes is particularly attractive because the first cladding layer for the ARROW core is made of SiN as well, and provides a natural approach to incorporating a nanopore with optical waveguides.

We have demonstrated that nanopores can be formed or drilled into our hollow-core channels with 1 μm thick top walls using FIB. FIG. 19 illustrates a) nanopores drilled in UCSC/BYU hollow channels, d) close-up showing three pores with d=500, 200, and 100 nm in $SiO_2$ top wall, respectively. FIGS. 19a) and 19b) show pores of varying size that we recently fabricated in such ARROW-like structures at the MRL Microscopy and Microanalysis Facility at UC Santa Barbara. Only the largest pore (d=500 nm, on left) reaches through the oxide layer. The Figure indicates, however, that pores can be drilled at pre-determined locations in hollow-core structures.

Micron-scale pores for cell flow cytometry can be etched into waveguides using conventional lithography and etching.

Ribosomes

While earlier work on ribosome structure was directed towards deducing ribosome structure from biochemical probing and x-ray crystallography, emphasis is now starting to shift towards the dynamics of the translation process and the movement of the ribosome parts. Hydroxyl radical probing was used to identify locations and arrangements of various ribosomal proteins, inter-atomic distances between tRNAs were determined, position and orientation of translation factors were measured, and the coupled movement of mRNA and tRNA during translation was studied using "toeprinting." Lancaster, L., et al., *RNA.* 6, 717-29, 2000; Lieberman, K. R., et al., *J Mol Biol.* 297, 1129-43, 2000; Wilson, K. S., et al., *Nat Struct Biol.* 7, 866-70, 2000; Hartz, D. et al., *Genes Dev.* 3, 1899-912, 1989. In addition, the crystal structure for the complete ribosomes was determined with 5.5 A resolution. Yusupov, M., et al., *Science.* 292, 883-896, 2001. Here, the focus is on recent results that are relevant to optical studies of individual ribosomes.

Ribosome labeling. Being able to label different parts of the ribosomes with fluorescent dye is essential for carrying out fluorescence studies. For FRET, two different molecules (donor and acceptor) need to be placed in close proximity to each other. Doubly fluorescent-labeled ribosomes will be constructed using an in vitro reconstitution strategy similar to the one that was used successfully in earlier tethered Fe(II) directed hydroxyl radical probing studies. Culver, G. M. and H. F. Noller, *Methods Enzymol.* 318, 461-75, 2000. In this strategy, single cysteine residues are introduced into non-conserved surface positions on individual ribosomal proteins by site-directed mutagenesis. The mutant proteins are overexpressed, purified and derivatized with a fluorescent dye, and then reconstituted into ribosomal subunits in vitro, together with the other non-labeled proteins and ribosomal RNA. Using the system for overexpression and FPLC purification of recombinant ribosomal proteins, large (~10 mg or more) amounts of individual purified proteins can readily be producde for derivatization with fluorescent probes and in vitro reconstitution of doubly-labeled ribosomes. Culver, G. M. and H. F. Noller, *Methods Enzymol.* 318, 446-60, 2000. So far, single-cysteine substitutions have been made at 18 different positions in 9 different ribosomal proteins. Several of these mutant proteins have been derivatized with fluorescent donor and acceptor probes (fluoresceine and tetramethyl-rhodamine in trial experiments), and successfully reconstituted functionally active, doubly-labeled ribosomes in vitro. The emission signals for these dyes peak around 530 and 580 nm, respectively. FRET was observed from the 30S subunit. So far, enough different cysteine-substituted protein positions have been synthesized to provide more than 20 different donor-acceptor pairs whose intermolecular distances are potentially useful for ribosome dyamics experiments, including Cy3 and Cy5.

Figure 21:
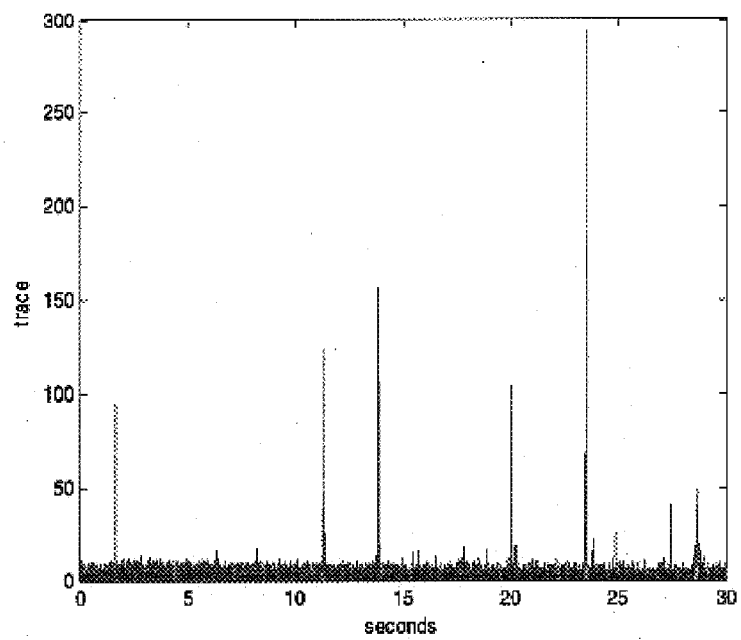
FIG. 21 illustrates time dependent detector bursts from small number of FITC-labeled ribosomes in inverted microscope setup.

Fluorescence measurements. The fluorescence from labeled ribosomes is studied using the conventional 3D inverted microscopy setup to observe fluorescence from small sample amounts using an avalanche photodetector in photon counting mode. FIG. 21 shows time-dependent detector bursts from fluorescently (FITC) labeled ribosomes excited with an Ar-ion laser in an inverted microscope setup. For this concentration (20 nM), the photon counts indicate nearly single particles within the excitation volume. We are in the process of optimizing the laser setup and the ribosome environment in order to unequivocally demonstrate single-ribosome detection in this bulk setup.

Figure 22:
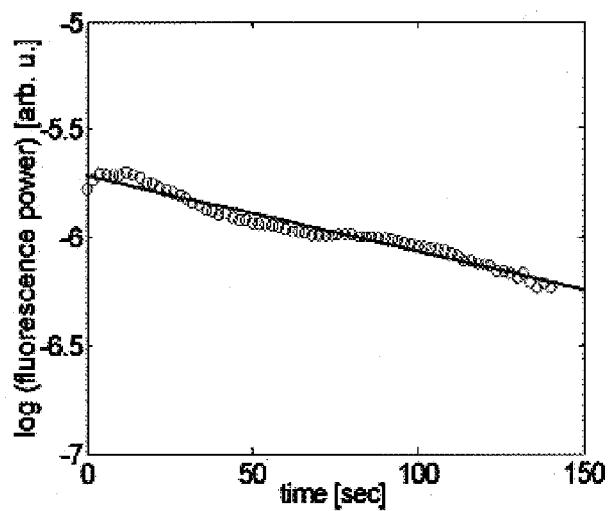
FIG. 22 illustrates time dependent fluorescence signal from fluorescently labeled ribosomes in ARROW waveguides indicating photobleaching of the Cy5 dye (concentration: 950 pM, circles: data, line: exponential fit).

ARROW waveguides have been used to study active ribosomes (E. coli) that were unspecifically labeled with Cy5 dye (spectra identical to Alexa 647). The ribosome preparation followed established protocols. For the labeling with Cy5 dye, the individual small and large subunits were activated at 42° C. for 10 minutes, and then associated at 37° C. for 10 minutes. The 70S ribosomes (final concentration 7.5 µM) were obtained and labeled in 50 mM Hepes, pH 7.6, 20 mM $MgCl_2$, 100 mM KCL, 1 mM TCEP in the presence of 375 µM Cy5-maleimide at 37° C. for 40 minutes. Ribosomes were purified of unbound dye and 30S subunits by centrifugation in sucrose gradient. Ribosomes were concentrated and washed of sucrose using Centricon with 100 kDa cut off. The labeling ratio was measured as 1.15 dye molecule per ribosome and the sucrose content was increased to 40% to avoid rapid evaporation from the currently open ARROW cores. Single-channel ARROWs (3.5 µm×15 µm×5 mm cores) were filled with the solution and fluorescence was excited and collected as shown in FIG. 15a. FIG. 22 illustrates time dependent fluorescence signal from fluorescently labeled ribosomes in ARROW waveguides indicating photobleaching of the Cy5 dye (concentration: 950 pM, circles: data, line: exponential fit). FIG. 22 shows the observed fluorescence signal as a function of time, showing a gradual decay that corresponds to the well-known photobleaching of Cy5 dye. A control sample without ribosomes showed no detectable signal. The ribosome concentration was 950 pM, corresponding to 150,000 ribosomes in the core for this first experiment. More detailed studies as a function of concentration and using intersecting waveguides are currently under way.

This constitutes the first demonstration of the use of integrated ARROW waveguides for sensing of functional biomolecules in a natural environment and is a promising and essential step towards use of these waveguides as a biomedical instrumentation tool.

The previous sections have demonstrated that all components for integrated sensors with single molecule sensitivity are in place. ARROW waveguides provide the required optical guiding, and can be fabricated in various shapes and lengths, specifically in two-dimensional arrays. They can be integrated with microfluidic reservoirs and were used to detect fluorescence at the level of single dye molecule sensitivity as well as from a single active biomolecule in buffer solution. Synthetic nanopores can successfully be formed or drilled in ARROW-like structures and have been shown by others to deliver current blockade signals. Finally, different components of the ribosome machine can be labeled and be detected in integrated waveguides.

Sensitivity limits and electrical control in integrated ARROW waveguides are discussed, in which ARROWs with liquid and solid core are interconnected with each other at 90 degrees. In order to determine the sensitivity limit of the intersection ARROW waveguides, we performed concentration-dependent fluorescence measurements on waveguides with open liquid cores as shown in the SEM image in FIG. 1a. As illustrated, fluorescence of Alexa 647 dye molecules in the mode excitation volume at the intersection (~100 fl) is excited by a HeNe laser coupled into the solid-core waveguide, and detected by avalanche photodiode in single photon counting mode (SPCM, Perkin Elmer) at the output of the liquid core. FIG. 1b shows the average detected photon counts per second as a function of the average number of molecules inside the mode excitation volume. The symbols show different experimental runs and the error bars reflect the estimated variation due to sample alignment. It can be seen that within the measurement uncertainty, we are capable of distinguishing between zero and one molecule within the excitation volume, demonstrating single molecule detection in integrated, planar ARROW waveguides.

Single-molecule Sensitivity in ARROW Waveguides

The present invention provides a device or method to incorporate synthetic nanoscale pores into an instrument that can detect a wide range of analytes, including nucleic acids, proteins, ribosomes, and viruses. The instrument incorporates a novel chip-based technology that will permit a portable device to be manufactured for both laboratory and field applications. The core technology is a sensor that incorporates a micron-scale ARROW microfluidic compartment which is cross-illuminated with exciting light from a laser source. (ARROW=antiresonant reflecting optical waveguide. See FIG. 17a.)

FIG. 17a illustrates a liquid core ARROW waveguide with a solid core waveguide crossing from left to right. The solid state waveguide allows laser illumination of a small volume within the liquid. FIG. 23b is a closeup view of the ARROW. The internal dimension is approximately 5 micrometers, and the layers of silicon nitride and silicon oxide that act as an ARROW waveguide are visible in the cross section.

Integrated ARROW waveguides can be fabricated in a completely monolithic process that does not require any wafer bonding steps and is fully compatible with conventional CMOS fabrication. A nanopore is used as a gate to guide single analyte particles into the laser excitation volume. As each particle passes through the illuminated femtoliter volume by electophoretic flow, a fluorescent marker on the particle emits photons, and these are collected by the waveguide and sent by fiber optics to an avalanche photodiode detector. See FIG. 30. FIG. 30 illustrates the integrated nanopore waveguide sensor for single molecule studies. As individual molecules tagged by a fluorescent probe are transported by microfluidics from the fluid reservoir through a nanopore and into the ARROW waveguide, each molecule in turn is illuminated by one or more optical fibers carrying laser light. The photons of emitted fluorescence are collected by fiber and delivered to an avalanche photodiode detector where they are counted. The spectral properties of the fluorescence probe identify each tagged molecule.

Figure 23:
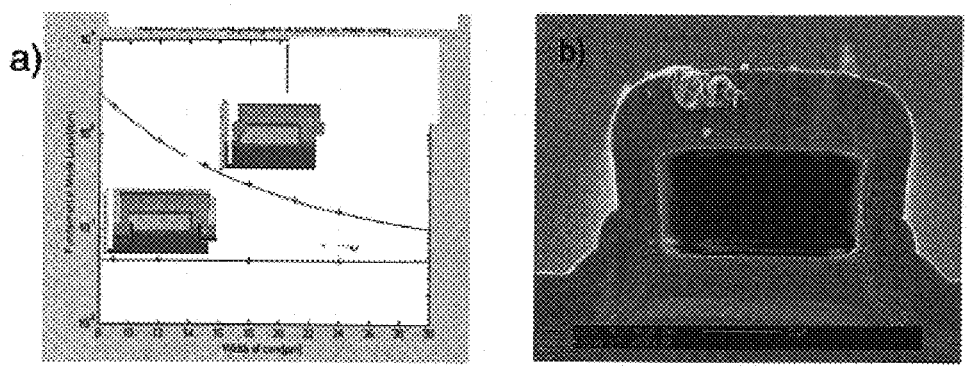
FIGS. 23(a) and 23(b) illustrate a) ARROW loss dependence on lateral structure; b) SEM image of fabricated test structure incorporating pre-etched silicon substrate.
Figure 31:
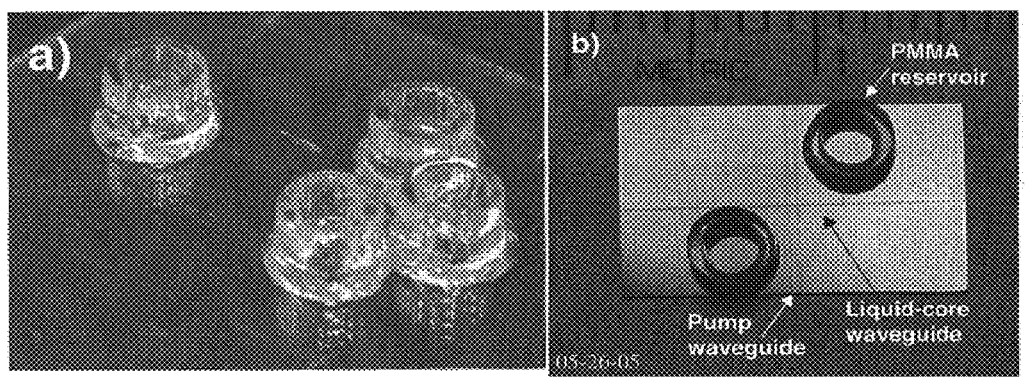
FIGS. 31(a) and 31(b) illustrate a) PMMA cylinders on glass electrophoresis separation device. b) Integration of PMMA fluidic reservoirs with ARROW waveguides

The uniqueness of the ARROW principle lies in the fact that we are able to guide light through picoliter volumes over large distances (order of centimeters) on the chip. This is possible because we fabricated waveguides in micron-sized cross sections using a specially designed dielectric multilayer sequence around the liquid channel (FIGS. 23 and 31). The particle also produces a characteristic blockade of ionic current through the pore that is used as additional information about the particle size and identity. A dedicated chip analyzes the current blockades and emitted photons, then counts, identifies and records each particle. Because it is entirely chip-based and uses microfluidic delivery of analyte samples, the integrated nanopore waveguide sensor instrument will be relatively inexpensive compared to other single molecule detection methods. All optical beam paths are confined to the plane of the chip, so there is no need to use bulky and expensive microscopes to resolve individual molecules.

Integrated structures using ARROW waveguides are already close to producing the sensitivity to reach the single molecule detection limit. Nevertheless, the optical waveguide and the system for making parallel optical and electrical measurements will achieve single molecule detection from dye molecules in a liquid core waveguide. Single molecule sensitivity will first be demonstrated by dilution of the dye solution in a single waveguide, and subsequently simultaneously from multiple waveguides on a single chip. This will be achieved using the following approaches.

Waveguide loss, coupling, and filtering. Low waveguide loss is the most essential requirement for reaching single-molecule detection and increasing the signal-to-noise ratio in future applications. FIG. 23 illustrates a) ARROW loss dependence on lateral structure; b) SEM image of fabricated test structure incorporating pre-etched silicon substrate. FIG. 23a shows how the waveguide loss can be reduced significantly for smaller core widths if the top layers are located below the sides of the core. This will allow us to reduce the core width and consequently the excitation volume. FIG. 23b shows first results for a test structure in which this principle is implemented. As can be seen, the difference to previous ARROW structures is that the silicon substrate was pre-etched into a pedestal shape using an isotropic plasma etch before the top ARROW layers were grown. This has the desired effect of lowering the top layers sufficiently so that the core is surrounded by air on three sides. The structure shown here was grown for fabrication test purposes. Its refractive indices and layer thicknesses were not optimized for low waveguide loss. We will fabricate optimized structures and measure the waveguide loss as before. D. Yin et al., *Applied Physics Letters,* 85, 3477, 2004; D. Yin et al., *Optics Express,* 12, 2710, 2004. We will also explore more anisotropic dry etching to produce more vertical sidewalls in the pre-etched Si substrate.

Secondly, we will study the radiation coupling efficiency of a dipole in the ARROW core as a function of orientation and location. FIG. 16b showed a good match between calculated and observed coupling efficiencies for one type of sample. We will expand the coupling efficiency simulations to be able to design optimized waveguides for both pump transmission and fluorescence collection.

In addition, we will demonstrate the integrated wavelength filter function of the ARROW waveguide that was discussed above by determining the waveguide loss at different wavelengths. We will measure the wavelength dependent loss over a large spectral range using a tunable laser source and compare the observed dispersion with our theoretical expectations.

Single molecule sensitivity: Several approaches can be taken to reduce the number of detectable molecules from 40 to 1 such as: reduction of the waveguide loss through pre-etching of the silicon substrate as described above; reduction of the excitation volume in the intersection geometry, and improvement of the detection setup.

The detection setup was improved by incorporating a more sensitive single photon avalanche detector (Perkin Elmer). This was sufficient to demonstrate single molecule fluorescence detection sensitivity in integrated ARROW waveguides (D. Yin et al., submitted to Optics Letters). Using two of these detectors in photon counting mode, single molecule detection can be verified in a Hanbury-Brown-Twiss intensity correlation measurement. Hollars C W et al., *Chemical Physics Letters,* 370, 393-8, 2003; Basche T et al., *Experimental Technique of Physics,* 41, 197, 1995.

The excitation volume in the intersection geometry is given by the product of the core cross section and the width of the solid-core waveguide. After improving the waveguide loss, the liquid-core width can be reduced from 12 µm to at least 9 µm. The core height will be reduced from 5.8 to 3-4 µm, but needs to remain large enough to ensure good fiber coupling at the output. The solid-core width can be reduced by a factor of 3 from 15 to 5 µm. In fact, our calculations show that this width will optimize the coupling of the excitation beam from single-mode fiber into the fundamental mode of the solid-core waveguide. This corresponds to a volume reduction by a factor of 6-7 which translates directly into a reduction of the number of excited molecules.

A combination of three approaches will make single molecule detection even easier than in the already demonstrated implementation and most importantly, will allow to achieve this level of sensitivity for various levels of integration: first using open channels with intersecting waveguides as described above, then in ARROW structures with integrated fluidic reservoirs (see FIG. 13b), and finally from multiple channels in parallel on the same chip.

Integration of Nanopore with ARROW Sensor

The second major goal will be the integration of the nanopores with the ARROW waveguides to enable controlled insertion and translocation of single molecules through synthetic nanopores into the waveguide channel. Because both ARROW and nanopore technologies rely on the same material (silicon nitride), their integration has a natural affinity. In addition, the diameters of prokaryotic ribosomes (20 nm for *E. coli*) are a perfect match for the capabilities of synthetic pore fabrication technology. Integration needs to address the opening of a nanopore on the ARROW waveguide, provision of suitable fluidic connections for introduction and extraction of biological material in solution, and placement of electrical connections to promote the directional movement of the sample molecules through the waveguide core.

We have shown that ARROW waveguides can be used to guide light through small volumes of liquid solution on a chip, that biological and synthetic nanopores can provide single molecule resolution through electrical measurements, and that the translation mechanism in ribosomes is a rich and relevant area for research in molecular biology that can benefit from optical studies on the single molecule level.

The present invention will combine these areas into a coherent program on optical and electrical sensing of single biomolecules on a chip. We will work towards building a fully integrated sensor whose implementation is shown in FIG. 30. Such a sensor will provide electrical (e.g., hairpin-DNA formation energy) and optical (e.g., conformational dynamics) sensing capabilities, and enable additional functionality via simultaneous use of electrical and optical signals. Liquid-core ARROW waveguides are integrated on a silicon chip for single molecule fluorescence sensing. Excitation (blue) and fluorescence (red) paths run in the sample plane and are accessible with fiber optics. Fluid reservoirs and electrical contacts are integrated on the chip as shown. A nanopore is placed at one end of the hollow core and fulfills a dual purpose. First, it produces current blockade signatures for analysis of biomolecule translocation through the pore. Secondly, it acts as a controllable gate for introduction of individual molecules into the optical sample volume enabling single molecule fluorescence at the waveguide junction. Many waveguide channels can be integrated on one wafer to build highly parallel two-dimensional optical and electrical sensor arrays.

Fluid delivery and flow characterization. So far, liquid has been introduced into the ARROW cores from the end facets using capillary forces. In an integrated device, control of the liquid and molecules therein will be done using electrically induced fluid flow. The overview picture in FIG. 30 and FIG. 31b show the envisioned fluidic and electrical connections and the first realization of such a structure, respectively. PMMA cylinders acting as fluid reservoirs are placed over openings in the ARROW waveguides. Duffy D. et al., *Analytical Chemistry* 70, 4974-4984, 1998; Monahan J., *Analytical Chemistry,* 73, 3193-3197, 2001; McDonald J. C. and Whitesides G. M., *Accounts of Chemical Research,* 35, 491-499, 2002). PMMA cylinders of the correct size have been fabricated and integrated with hollow channels made of $SiO_2$ to demonstrate electrophoretic separation of amino acids as well as with integrated ARROW structures (FIG. 31b). B. A. Peeni et al., *Lab on a chip,* 5, 501-505, 2005. It is important to point out that the electroosmotic flow component in these ARROW waveguide structures is expected to be small as the liquid core is surrounded by silicon nitride and not $SiO_2$. R. M. Guijt et al., Electrophoresis, 22, 235-241, 2001.

Electrophoretic movement of ribosomes and other biomolecules (e.g., proteins or DNA) through ARROW structures will be demonstrated. The first approach will be to insert electrical probes directly into the PMMA reservoirs to apply the drive voltage. B. A. Peeni et al., *Lab on a chip,* 5, 501-505, 2005. Another integration step will be added by depositing electrical contact pads on the structure as shown in FIG. 30. Due to the compatibility of the fabrication process with standard silicon IC-technology, this can be accomplished by an additional photolithography step. For neutral molecules, additional contacts could be deposited on top of the waveguide to enable dielectrophoretic movement. AC electrophoresis will be used to hold a molecule at the location of the waveguide intersection. We will characterize the electrical parameters required and the resulting molecule velocities. The latter, in particular, will provide important design parameters for the time-resolved ribosome studies described below.

Incorporation of nanopore in ARROW waveguide. FIG. 24a) shows the front view of the drilled test pores. In the Figure, only the large hole on the left extends all the way through the 1.25 μm thick $SiO_2$ top layer. For straight walls, the aspect ratio of pore diameter to etch depth (layer thickness) must be approximately one. Therefore, the pore needs to be etched in the first nitride layer above the core of an ARROW waveguide.

Figure 20:
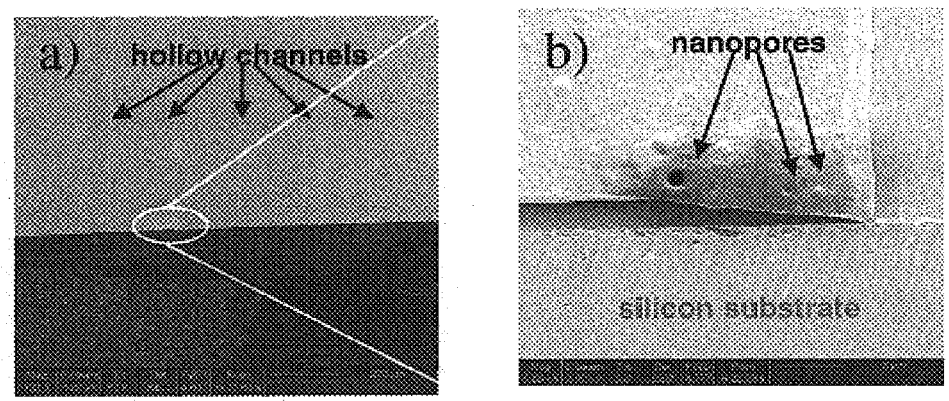
FIG. 20(a) and (b) illustrate a) Nanopores formed or drilled in UCSC/BYU hollow channels, b) close-up showing three pores with d=500, 200, and 100 nm in $SiO_2$ top wall, respectively.
Figure 24:
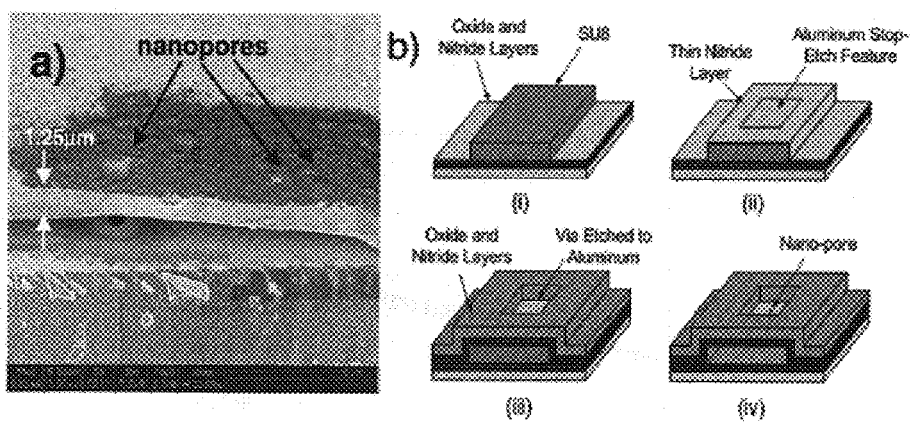
FIGS. 24(a) and 24(b) illustrate a) Front view of test pores (see FIG. 15); only the largest one reaches through the entire wall. b) Fabrication sequence for nanopore integration with hollow ARROW waveguide.

FIG. 24 illustrates a) Front view of test pores (see FIG. 20); only the largest one reaches through the entire wall. b) Fabrication sequence for nanopore integration with hollow ARROW waveguide. FIG. 24b) shows the proposed fabrication sequence to accomplish this. After deposition of the sacrificial SU8 core and first top ARROW layer (i), a thin aluminum layer will be deposited (ii), followed by PECVD growth of the remaining ARROW layers. Subsequently, a well will be formed by $CF_4$ plasma etching, terminating at the aluminum layer (iii). The SU8 core and aluminum will be removed by acid etching exposing the top nitride layer. Nanopores of various sizes centered around the average ribosome diameter of 20 nm will then be formed using standard FIB and reflow techniques (iv). During testing, molecules and solvents will then enter from the top of the waveguide and flow laterally along its core. The final step will be etching the nanopore using a focused ion beam. The pore dimensions will be characterized in situ with the UCSB dual-beam FIB instrument and with the scanning microscope (AFM).

The pores will then be tested for electrical detection of translocation of single ribosomes using the nanopore characterization setup. These measurements will provide the first nanopore studies on ribosomes and will also yield the first demonstration of integration of a nanopore with another (optical) sensor. Other biomolecules will be studied, for example, DNA, using a combination of current blockade measurements in synthetic nanopores and optical excitation in ARROW waveguides on a chip.

Single-ribosome Studies in Integrated Waveguides

A further goal of the present invention is to demonstrate the applicability of the ARROW-based single-molecule detection to the study of fundamental problems in molecular biology, in particular the dynamics of translation in the ribosome. Ultimately, we envision that single ribosomes will be introduced into the liquid-core waveguides from fluidic reservoirs or fluidic channels from other parts of a larger analysis system. Introduction would occur through a synthetic nanopore of approximately 20 nm diameter in the silicon nitride layer surrounding the ARROW core. Detection of the current blockade will signal the entry of the molecule into the waveguide and can be used to synchronize optical probing and other events, e.g., introduction of other materials such as messenger RNA (mRNA) into the channel. In this application, it is proposed to demonstrate the components required to realize this vision and develop the method to observe time-resolved FRET from single ribosomes. The following subsections discuss the required milestones in more detail. It is important to note that results from most of the experiments to be described below can be transferred directly to sensing of other biomolecules in the waveguide core.

Figure 25:
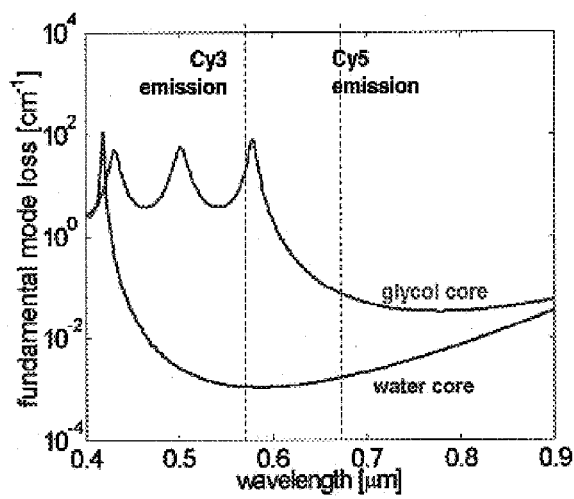
FIG. 25 illustrates wavelength-dependent loss for pre-etched ARROW with current cladding layer thickness values.

Waveguide optimization for ribosome studies. We intend to study the ribosome as a particular biomolecule using fluorescence resonance energy transfer (FRET). So far, all fluorescence measurements using ARROWs were carried out with a single fluorophore. Consequently, they required optimization of the liquid-core structure for only a single wavelength. For FRET, on the other hand, we need to be able to collect fluorescence signals from both the donor and acceptor molecule. G. Haran, *J. Phys.,* 15, R1291-R1317, 2003. Therefore, we need to ensure that the wavelength response of the waveguide is designed for this case. One donor/acceptor pair we intend to use is that of Cy3/Cy5 (equivalent to Alexa 555/647) with respective emission wavelengths of 565 and 660 nm. FIG. 25 shows the wavelength-dependent loss calculated for an pre-etched ARROW structure with the currently used cladding layer thicknesses and water (n=1.33) and ethylene glycol (n=1.43) in the core, respectively.

It can be seen that the loss is low at 660 nm in both cases. However, light at the shorter wavelength does not propagate well through a water-filled core in the current design. Using the design rules described in H. Schmidt et al., *IEEE Journal of Selected Topics in Quantum Electronics,* 11, 519, 2005 we will design and test ARROW structures whose wavelength response is optimized for different FRET donor/acceptor pairs in water-like cores (nC~1.33).

Ribosome adhesion to the waveguide walls. Attachment of ribosomes to the ARROW waveguide walls could present a serious problem for carrying out fluorescence measurements because fluorescence coupling to the waveguide mode is most efficient for molecules in the center of the core. This is especially true for single-ribosome detection where signal-to-noise ratios will be low.

We have already succeeded in observing ribosome fluorescence in ARROWs which indicates that many molecules do not stick to the walls. In addition, it is known that proteins and other biomolecules show reduced interactions with silicon nitride compared to silica. R. M. Guijt et al., *Electrophoresis,* 22, 235-241, 2001. This is yet another big advantage of using silicon nitride as the first ARROW cladding layer. We therefore expect that ribosome adhesion will not play an important role in our experiments.

However, we have not quantified this effect and propose to do so with further experiments. To this end, we will introduce ribosomes at higher concentration in the ARROW core such that the emitted fluorescence can be imaged with our CCD camera (Photon Inc.) as shown in FIG. 15. We will then model the observed spatial intensity distribution to various distributions of radiating dipoles in the core using our software package from Photon Design. If wall adhesion occurs preferentially, the intensity will be distributed in a different pattern across the core. Should this be found to be the case, we will explore the possibility of coating the walls with a thin layer that prevents adhesion, and we will investigate the effect of such a wall coating on the optical properties of the ARROW waveguide.

Figure 26:
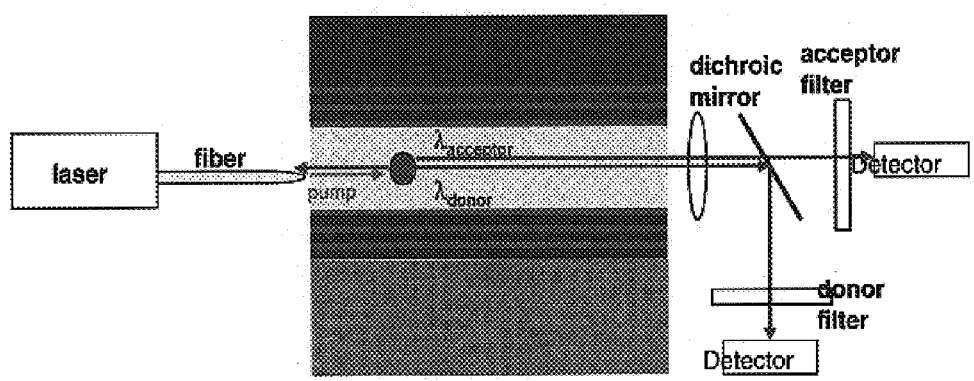
FIG. 26 illustrates setup to detect FRET from a bulk sample of ribosomes.

"Bulk"-FRET in current waveguides. As discussed in section above, fluorescence from labeled ribosomes in ARROW waveguides has been successfully detected. Based on these results, our next step will be to demonstrate the capability of measuring FRET in the same setup and subsequently in structures as shown in FIG. 31b. To this end, we will investigate different FRET donor/acceptor pairs in ARROW waveguides that are optimized for guiding at the respective emission wavelengths. These pairs will include FITC/Rhod-2, Cy3/Cy5, and Alexa555/Alexa647. Excitation will occur with a tunable continuous wave laser (Coherent Inc.) or with femtosecond pulses from the tunable parametric oscillator in the Schmidt lab (Coherent Inc., 510-700 nm tuning range). The detection setup shown before in FIG. 15 will be modified by adding a beam splitter or dichroic mirror as shown below in FIG. 26 that allows for simultaneous detection of donor and acceptor emission using the appropriate filters in the two split paths. A similar setup was already used to analyze the fluorescence collection efficiency of the ARROW waveguides, submitted to Applied Physics Letters and only the correct filters are required to implement this modification. D. Yin et al., *Highly efficient fluorescence detection in picoliter volume liquid-core waveguides*. This measurement will first be done with the current open channel structures and later with included fluidic reservoirs. FIG. 26 illustrates setup to detect FRET from a bulk sample of ribosomes.

We point out that "bulk" in this context refers to ribosome concentrations of 1 nM and approximately $10^5$ ribosomes in the waveguide.

Ribosome labeling. The capabilities for providing more than 20 different donor-acceptor pairs has been developed with potentially useful intermolecular spacings based on cysteine-substituted proteins. FRET was demonstrated with the fluoresceine/tetramethylrhodamine pair (FITC/Rhod-2, 520/576 nm). Within this project, labeling with other FRET pairs will be carried out and tested. In particular, we will focus on the Cy3/Cy5 and Alexa555/Alexa647 pairs. Both have emission wavelengths around 565/660 nm. However, the Alexa family exhibits better fluorescence properties, in particular higher photostability, and is therefore a better candidate for single-molecule FRET detection. www.probes.invitrogen.com.

Ribosome detection through synthetic nanopore. We will test whether individual labeled ribosomes can be transported through a synthetic nanopore and be detected using optical microscopy. This will first be done by the Deamer group using the Agilent nanopore chip and the bulk setup based on an inverted microscope as described above. This has the advantage that detection of single silica spheres was already demonstrated and transition to the nanopore/ribosome case can occur rapidly.

These measurements will provide important feedback for the translocation behavior of the ribosome without the added complication of first integrating the pore with the ARROW chip.

Single-ribosome fluorescence. The conclusion from the ARROW fluorescence measurements to date was that sensitivity is highest and can reach the single molecule limit if orthogonally intersecting pump and collection waveguides are used. We will use this geometry to detect fluorescence from single ribosomes after having established ARROW sensitivity to single dye molecules and "bulk" FRET.

A preferred embodiment of the experimental method will be to introduce the ribosome through the nanopore gate using electrophoresis and use the electrical current blockade signal as an indicator of molecule entry into the core. The molecule will then be excited by the pump laser as it passes the intersection and fluorescence will be detected in the usual way. If the nanopore works well, the electrical signal should be helpful in analyzing and eliminating spurious background photon counts on the optical detector. It should also be possible to determine the velocity of the ribosome in the channel by correlating the detection times of optical and electrical signals. This would be the first demonstration of enhancing single molecule studies through simultaneous use of electrical and optical detection.

Time-resolved single-ribosome FRET. Finally, we will develop the capability of detecting time-resolved FRET to study the dynamics of translation of the genetic code to answer some of the questions that were mentioned in the introduction. FRET pairs can be placed in different parts of the ribosome including head and body of the 30S subunit, platform and body, and different positions of mRNA and tRNA (e.g., elbow region). We will focus on monitoring FRET generated within the 30S subunit upon association of 30S and 50S subunits. These pilot studies will pave the way for investigating more controversial processes in the future.

Figure 27:
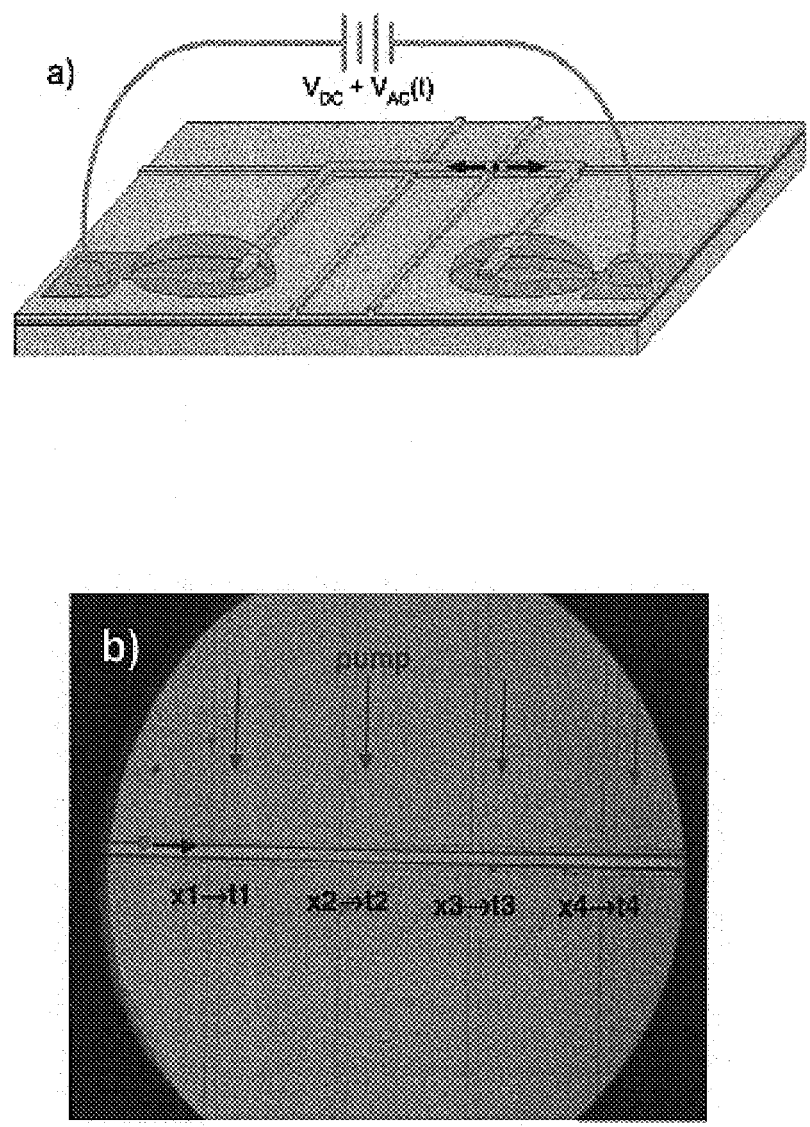
FIGS. 27(a) and 27(b) illustrate ribosome localization approaches: a) an AC electric field is turned on once the molecule reaches the waveguide intersection; b) the molecule is probed at various locations along the channel; each probe location corresponds to a different excitation time.

In contrast to other recent FRET studies on ribosomes, our measurements will be on freely moving ribosomes that are not immobilized on a surface. S. C. Blanchard et al., *PNAS* 101, 12893-12898, 2004; S. C. Blanchard et al., *Nature Structural & Molecular Biology*, 11, 1008-1014, 2004. In order to carry out time-dependent studies, the ribosome must, of course, be localized in an excitation volume for a sufficiently long period of time. To ensure this, we will pursue two approaches as shown in FIG. 27a) and 27b) below. FIG. 27 illustrates ribosome localization approaches: a) an AC electric field is turned on once the molecule reaches the waveguide intersection; b) the molecule is probed at various locations along the channel; each probe location corresponds to a different excitation time.

The first is to move the ribosome along the ARROW channel using DC electrophoresis. Once it reaches the intersection shown in FIG. 27a it is excited by the pump laser and fluorescence is detected. This signal will be used as a trigger to turn off the DC field and turn on a low-frequency AC electric field. The purpose of the AC field is to keep the ribosome within the excitation volume (length ~5 μm) for the duration of the FRET measurement. Here, the ribosome will be dynamically localized.

The second approach is to make use of the parallel excitation capability of the ARROW waveguide that was already demonstrated above. Here, we propose to use spatio-temporal mapping to achieve time resolution for the FRET detection. As shown in FIG. 27b, the ribosome would move through the ARROW using DC electrophoresis. However, it would be probed at different points along its trajectory. These different space points can be mapped onto a time axis using the velocity of the molecule in the channel (xi→ti). Since the genetic translation process in the ribosome is relatively slow (~60 ms for adding a single amino acid to a growing protein), a time resolution below this value can be achieved. J. Frank, *Chemistry and biology*, 7, R134, 2000. For example, a resolution of 5 ms for waveguides spaced by 20 μm would require a channel velocity of 0.4 cm/s. We will use the results of our microfluidic characterization experiments to assess and optimize this approach. In addition, waveguide losses due to different optical path lengths and multiple intersections will be measured and taken into account. We point out that this concept of spatio-temporal mapping is only afforded by the highly integrated nature of the ARROW waveguides.

The experiments described in this subsection would constitute the first dynamic optical studies on freely moving ribosomes and open the way for a detailed look at many aspects of translocation.

DNA Hybridization Detection

The first experiment that utilizes optical waveguiding in conjunction with the nanopore will be hybridization detection of single molecules. A single DNA strand will be introduced in the ARROW core through the hemolysin nanopore. Entrance of the molecule is monitored by observation of a current blockade. The core will contain molecules with the matching base pair sequence and TO-PRO dye. These can be introduced in advance from the other end of the core. Upon hybridization, fluorescence from intercalated dye can be observed. This measurement will combine the gating properties of the nanopore and the fluorescence sensing characteristics of the ARROW. In addition, the measurement will be carried out on several channels in parallel. These can be filled with different oligonucleotides and fluorescence will only be observed from the channel that contains the correct sequence. This will be a demonstration for rapid, parallel nucleotide identification.

DNA Sequencing

A large part of the promise of single molecule studies lies in the potential for rapid, high-throughput sequencing of genomic DNA at rates of thousands of base pairs per second (bp/sec). Several approaches using single molecule fluorescence are being pursued. J. Joannopoulos et al., *Photonic Crystals*, Princeton, 1995; Y. Fink et al., *Science*, 282, 1679, 1998; P. Yeh et al., *J. Opt. Soc. Am.*, 67, 423, 1977; G. R. Hadley et al., *Opt. Lett.*, 29, 809, 2004; P. Russell, *Laser Focus World*, 38, 77, 2002; H. F. Noller et al., *FEBS Letters*, 514, 11-16, 2002. They are based on labeling DNA with fluorophores followed by anchoring the DNA molecule in a flow stream using optical tweezers or micropipettes. J. Joannopoulos et al., *Photonic Crystals*, Princeton, 1995; Y. Fink et al., *Science*, 282, 1679, 1998; H. F. Noller et al., FEBS Letters, 514, 11-16, 2002; G. R. Hadley et al., *Opt. Lett.*, 29, 809, 2004; P. Russell, *Laser Focus World*, 38, 77, 2002. Then, an exonuclease enzyme is used to sequentially release fluorophore-tagged monomers which are the excited to fluoresce at an excitation spot. In order to enable complete sequencing, only two bases per strand (e.g., G and C) can be tagged at a time to yield two-pair sequences. By analyzing all six two-pair combinations, the complete sequence can be deducted. While promising, these optical approaches have suffered from limited detection efficiency and large amounts of noise. FIG. 28 illustrates a) DNA sequencing with nanopore device. b) Left: Hemolysin nanopore with λ-exonuclease. Right: Prolonged current blockade in presence of λ-exonuclease.

It is proposed to implement and improve this concept in the integrated nanopore/ARROW device. FIG. 28*a* shows the envisioned principle of the measurement. The nanopore controls the introduction of the ss-DNA strand to be sequenced into the ARROW core and eliminates the need for bead attachment, optical tweezers, and micropipettes. The reservoir above the (hemolysin or small synthetic) nanopore contains fluorescently tagged double stranded DNA and the enzyme λ-exonuclease, which digests ds-DNA into ss-DNA. Culver, G. M. and H. F. Noller, *Methods Enzymol.* 318, 461-75, 2000; M. Dorywalska et al., *Nucl. Acids Research*, 33, 182-189, 2005. While the enzyme itself is too large to move through the nanopore, the ss-DNA it produces is drawn into the pore. Use of this enzyme is required to slow the translocation rate from tens of thousands bp/sec to rates of ~100 bp/sec. This effect was recently demonstrated in the Deamer lab by observing prolonged current blockade signals (FIG. 28*b*). S. C. Blanchard et al., *PNAS* 101, 12893-12898, 2004. As the ss-DNA enters the ARROW core, it is rapidly cleaved into monomers by the enzyme *E. coli* exonuclease-I. S. C. Blanchard et al., *Nature Structural & Molecular Biology*, 11, 1008-1014, 2004. The monomers are transported electrophoretically to the waveguide intersection, where single molecule fluorescence is excited and collected as previously described. We will first verify that λ-exonuclease-processed DNA can be moved through the core and yield a measurable fluorescence signal. Subsequently, we will add exonuclease-I to produce fluorescing monomers.

This approach to optical sequencing combines all advantages of the nanopore/ARROW device in a unique measurement. The key components (DNA anchor, fluorescence detection) are integrated on a chip, and the electrical signal will be used to ensure proper operation. A significant advantage is that sequencing can be carried out in parallel channels simultaneously. All six two-base pair combinations can be analyzed in different channels simultaneously using the same excitation beam. This will speed up optical sequencing significantly and improve the signal-to-noise ratio. In addition, this method has the potential to be combined with sequencing based on electrical nanopore signals, further adding to the amount of available data and improving the reliability of the method. J. R. Grunwell et al., *J. Am. Chem. Soc.*, 123, 4295, 2001.

Protein Analysis.

The identification and measurement of certain proteins in blood is an important clinical tool. For instance, serum lipoprotein analysis is routinely used to diagnose risk of heart disease, chorionic gonadoropin is determined in pregnancy tests, and prostate specific antigen (PSA) is commonly used to scan patients for prostate cancer. Tests for blood proteins require 5 to 10 milliliters of blood obtained by venipuncture. They are also time consuming, so that often several days pass before a physician receives needed information. We believe that the nanopore/ARROW sensor instrument will be able to provide such information in minutes using just one drop of blood obtained by a finger lancet, as diabetics routinely perform on themselves.

Virus Detection and Identification.

Measurement of viral load in the blood of hepatitis and AIDS patients is an important clinical tool, both for diagnosing the disease and for monitoring response to therapy. Detection of certain pathogenic viruses and bacteria like anthrax are useful to reduce the risk factors in bioterrorism. Current methods for determining viral load are time consuming and expensive. We believe that our instrument will be able to provide such measurements to a physician in a few minutes at minimal cost.

Flow Cytometry of Small Volumes

Another area in which optical interactions with a liquid sample containing (pathogenic) biological material are studied is flow cytometry. This field is well developed and an advanced setup capable of individual particle analysis is shown in FIG. 29a. V. P. Maltsev, *Rev. Sci. Inst.*, 71, 243, 2000. FIG. 29 illustrates flow cytometry setups after V. P. Maltsev, *Rev. Sci. Inst.*, 71, 243, 2000 and D. Ivnitski et al., *Biosensors and Bioelectronics*, 14, 599, 1999. In both cases, light cannot be guided along the liquid channel and is detected in the perpendicular direction.

In this case, a microchannel containing the specimen with a width of 10 µm is used. A laser is sent into this channel and fluorescence is detected perpendicular to the excitation direction. The important facts to note are that no waveguiding within the microcuvette is involved, measurements of multiple channels are impossible with this setup and the whole setup is composed of bulk optics. Another example for a generic flow cytometry setup is shown in FIG. 29b.

In FIG. 29b, a liquid sample containing potentially pathogenic bacteria is passed through a flow cell and the specimen is excited using a microscope objective in the perpendicular direction. This arrangement brings with it significant loss of the optical signal due to multiple interfaces between the sample space and the end of the microscope objective. In addition, only one channel can be excited this way as the focal depth of the excitation spot is very small and the excitation beam diverges quickly after it passes the flow cell. Leistiko et al. describe another realization of a microfluidic channel system for biological and biochemical applications. Leistiko O and Jensen P F. [Conference Paper] *IOP Publishing. Journal of Micromechanics & Microengineering*, 8, 148-50, 1998. In this microfluidic channel system, optical fibers are placed in etched grooves on a silicon substrate and covered with a pyrex slide. The light from the optical fibers is coupled into integrated waveguides in the silicon. However, they intersect an ordinary microcapillary which again leads to significant coupling losses into and out of the capillary leading to a coupling efficiency of only a few percent.

Our instrument can achieve flow cytometry on a chip using a micropore to signal entry of individual cells and fluorescence from the ARROW waveguides for detection.

Conclusion

While the present invention has been described in connection with several presently preferred or illustrative embodiments, it is to be understood that other similar embodiments may be used or modifications and additions may be made to the described embodiments for performing the same functions of the present invention without deviating therefrom. For example, while exemplary embodiments of the invention are described as including ARROW waveguides, one skilled in the art will recognize that the present invention is not limited thereto, and that the methods described herein may apply to other implementations, and may be applied to any number of such devices and applications without departing from the invention. Therefore, the present invention should not be limited to any single embodiment, but rather should be construed in breadth and scope in accordance with the appended claims.

What is claimed:

1. An optical waveguide, comprising a substrate and multiple layers of solid state material disposed on the substrate, a non-solid core extending through at least one of the multiple layers, an intersecting waveguide portion for use in injecting light into said non-solid core, one or more antiresonant reflecting layers adjacent to the non-solid core whereby light is substantially prevented from leaking out of the channel in a transverse direction, and an electrical component in fluid communication with the non-solid core to control sample material movement through the non-solid core.

2. The optical waveguide of claim 1, wherein the electrical component is an electrophoretic or electroosmotic component.

3. The optical waveguide of claim 1, wherein the non-solid core may be used to contain the sample material whose light transmission, absorption, and/or interference characteristics are to be measured.

4. The optical waveguide of claim 3, further comprising a detector of light transmission, absorption, and/or interference characteristics.

5. The optical waveguide of claim 4 wherein the detector is an optical detector integrated with the optical waveguide on the substrate.

6. The optical waveguide of claim 5, wherein a single nucleic acid molecule, a single protein molecule, a single amino acid molecule or a single particle from the sample material is detected by the optical detector.

7. The optical waveguide of claim 4, wherein the detector is a fluorescence detector.

8. The optical waveguide of claim 4, wherein the detector is a light detector or a Raman scattering detector.

9. The optical waveguide of claim 1, wherein the sample material is nucleic acid, protein, or amino acid.

10. The optical waveguide of claim 9, wherein the nucleic acid, protein, or amino acid is separated from a mixture in the sample material.

11. The optical waveguide of claim 10, wherein a single nucleic acid molecule, a single protein molecule, a single amino acid molecule or a single particle is separated from the mixture.

12. The optical waveguide of claim 11, wherein a single nucleic acid molecule, a single protein molecule, a single amino acid molecule or a single particle is detected within the optical waveguide.

13. The optical waveguide of claim 1, wherein the sample material is a single molecule or a single particle.

14. The optical waveguide of claim 1, wherein the electrical component is a first electrode and a second electrode applying a current across a length of the non-solid core.

15. The optical waveguide of claim 14, further comprising a first reservoir and a second reservoir at opposite ends of the non-solid core in fluid communication with the non-solid core, the first reservoir in fluid communication with the first electrode and the second reservoir in fluid communication with the second electrode.

16. The optical waveguide of claim 14, wherein the electrodes are platinum.

17. The optical waveguide of claim 14, wherein the electrodes are silver/silver chloride.

18. The optical waveguide of claim 14, wherein the electrodes are microelectrodes integrated on the substrate.

19. The optical waveguide of claim 1, further comprising a nanopore or micropore in fluid communication with the non-solid core.

20. The optical waveguide of claim 19, wherein the nanopore or micropore is configured to limit passage of a sample material through the nanopore or micropore to a single molecule or particle at a time.

21. The optical waveguide of claim 20, wherein the single molecule or particle is a nucleic acid molecule, a polypeptide molecule, an amino acid molecule, or a ribosome.

22. The optical waveguide of claim 19, wherein the particle is one cell or one viral particle.

23. The optical waveguide of claim 19, wherein an electrical signal is generated upon passage through the nanopore of the single molecule.

24. The optical waveguide of claim 19, wherein an electrical signal is generated upon passage through the micropore of the single cell or viral particle.

25. The optical waveguide of claim 1, wherein the one or more antiresonant reflecting layers comprises a Fabry-Perot reflector or a Bragg mirror adjacent to the non-solid core.

26. The optical waveguide of claim 1, wherein the substrate comprises silicon (Si) and the multiple layers comprise $SiO_2$ and SiN.

27. The optical waveguide of claim 1, wherein the non-solid core has an index of refraction which is lower than the index of refraction of the surrounding solid-state material, and wherein light can be transmitted with low loss through the non-solid core.

28. The optical waveguide of claim 1, wherein the optical waveguide is generally structured as an anti-resonant reflecting optical waveguide (ARROW).

29. The optical waveguide of claim 28, wherein the one or more antiresonant reflecting layers is a Fabry-Perot reflector adjacent to the non-solid core.

30. The optical waveguide of claim 1, further comprising a perpendicular waveguide portion for use in injecting light into the non-solid core for measuring fluorescence characteristics associated with a sample material.

31. The optical waveguide of claim 1, wherein the non-solid core has a substantially square cross-section.

32. The optical waveguide of claim 1, wherein the non-solid core has a substantially rectangular cross-section.

33. The optical waveguide of claim 1, wherein the non-solid core has a substantially arched cross-section.

34. The optical waveguide of claim 1, further comprising a sample-injection port in fluid communication with the non-solid core for injecting the sample material into the non-solid core.

35. The optical waveguide of claim 34, wherein the sample injection port is oriented substantially perpendicular with respect to a longitudinal axis of the non-solid core.

36. The optical waveguide of claim 34, wherein the sample injection port is oriented above the non-solid core.

37. An optical waveguide generally structured as an anti-resonant reflecting optical waveguide (ARROW), comprising:
  a substrate and multiple layers of solid state material disposed on the substrate, and a non-solid core extending through at least one of the multiple layers, wherein the non-solid core has an index of refraction which is lower than the index of refraction of the surrounding solid-state material, and wherein light can be transmitted with low loss through the non-solid core;
  a Fabry-Perot reflector adjacent to the non-solid core, for substantially preventing light from leaking out of the core in a transverse direction;
  a perpendicular waveguide portion for use in injecting light into the non-solid core for measuring fluorescence characteristics associated with the sample material;
  a sample-injection port in fluid communication with the non-solid core for injecting a sample fluid into the non-solid core, the sample injection port being oriented substantially perpendicular with respect to a longitudinal axis of the non-solid core; and
  an electrical control component in fluid communication with the non-solid core to control movement of an analyte in the sample fluid through the non-solid core.

38. The optical waveguide of claim 37, wherein the non-solid core may be used to contain the analyte whose light transmission, absorption, and/or interference characteristics are to be measured.

39. The optical waveguide of claim 38, further comprising a detector of light transmission, absorption, and/or interference characteristics.

40. The optical waveguide of claim 39 wherein the detector is an optical detector integrated with the optical waveguide on the substrate.

41. The optical waveguide of claim 40, wherein a single nucleic acid molecule, a single protein molecule, a single amino acid molecule or a single particle from the sample material is detected by the optical detector.

42. The optical waveguide of claim 39, wherein the detector is a fluorescence detector.

43. The optical waveguide of claim 39, wherein the detector is a light detector or a Raman scattering detector.

44. The optical waveguide of claim 37, wherein the analyte is nucleic acid, protein, or amino acid.

45. The optical waveguide of claim 44, wherein the nucleic acid, protein, or amino acid is separated from a mixture in the sample material.

46. The optical waveguide of claim 45, wherein a single nucleic acid molecule, a single protein molecule, a single amino acid molecule or a single particle is separated from the mixture.

47. The optical waveguide of claim 46, wherein a single nucleic acid molecule, a single protein molecule, a single amino acid molecule or a single particle is detected within the optical waveguide.

48. The optical waveguide of claim 37, wherein the analyte is a single molecule or a single particle.

49. The optical waveguide of claim 37, wherein the electrical component is an electrophoretic component.

50. The optical waveguide of claim 49, wherein the electrical component is a first electrode and a second electrode applying a current across a length of the non-solid core.

51. The optical waveguide of claim 50, further comprising a first reservoir and a second reservoir at opposite ends of the non-solid core and in fluid communication with the non-solid core, the first reservoir in fluid communication with the first electrode and the second reservoir in fluid communication with the second electrode.

52. The optical waveguide of claim 50, wherein the electrodes are platinum.

53. The optical waveguide of claim 50, wherein the electrodes are silver/silver chloride.

54. The optical waveguide of claim 50, wherein the electrodes are microelectrodes integrated on the substrate.

55. The optical waveguide of claim 37 further comprising a nanopore or micropore in fluid communication with the non-solid core.

56. A measurement system, comprising:
  an optical waveguide comprising a channel surrounded by a solid-state material, including a Fabry-Perot reflector adjacent to the channel, whereby light is substantially prevented from leaking out of the channel in a transverse direction;
  a perpendicular waveguide portion for use in injecting light into the channel;
  means for injecting into the channel an analyte in a sample fluid;
  an electrical control component in fluid communication with the non-solid core to control movement of the analyte through the non-solid core; and
  means for measuring selected optical and electrical properties associated with the analyte in the sample.

57. The system of claim 56, wherein the selected optical properties include light transmission, absorption, interference and/or fluorescence characteristics associated with the sample material over macroscopic distances within the channel.

58. The system of claim 57, further comprising a detector of light transmission, absorption, and/or interference characteristics.

59. The system of claim 58 wherein the detector is an optical detector integrated with the optical waveguide on the substrate.

60. The system of claim 59, wherein a single nucleic acid molecule, a single protein molecule, a single amino acid molecule or a single particle from the sample material is detected by the optical detector.

61. The system of claim 58, wherein the detector is a fluorescence detector.

62. The system of claim 58, wherein the detector is a light detector or a Raman scattering detector.

63. The system of claim 56, wherein the analyte is nucleic acid, protein, or amino acid.

64. The system of claim 63, wherein the nucleic acid, protein, or amino acid is separated from a mixture in the sample material.

65. The system of claim 64, wherein a single nucleic acid molecule, a single protein molecule, a single amino acid molecule or a single particle is separated from the mixture.

66. The system of claim 65, wherein a single nucleic acid molecule, a single protein molecule, a single amino acid molecule or a single particle is detected within the optical waveguide.

67. The system of claim 56, wherein the analyte is a single molecule or a single particle.

68. The system of claim 56, wherein the electrical component is an electrophoretic component.

69. The system of claim 68, wherein the electrical component is a first electrode and a second electrode applying a current across a length of the non-solid core.

70. The system of claim 69, further comprising a first reservoir and a second reservoir at opposite ends of the non-solid core and in fluid communication with the non-solid core, the first reservoir in fluid communication with the first electrode and the second reservoir in fluid communication with the second electrode.

71. The system of claim 69, wherein the electrodes are platinum.

72. The system of claim 69, wherein the electrodes are silver/silver chloride.

73. The system of claim 69, wherein the electrodes are microelectrodes integrated on the substrate.

74. The system of claim 56 further comprising means for injecting light into the channel, wherein the injected light is guided within the channel and through the sample material.

75. The system of claim 56, wherein the channel has a length which is optimized for a desired range of wavelengths.

76. The system of claim 56, wherein the optical waveguide comprises a silicon (Si) substrate and multiple layers of solid state material disposed on the substrate, and a non-solid core extending through at least one of the multiple layers, whereby the non-solid core may be used to contain the sample material.

77. The system of claim 56 further comprising a nanopore or micropore, for injecting into the channel an analyte in a sample fluid.

78. The system of claim 56, wherein the nanopore is configured to limit passage of an analyte through the nanopore or micropore to one molecule or one particle at a time.

79. The system of claim 77, wherein an electrical signal is generated upon passage through the nanopore or micropore of the single molecule or single particle.

80. The system of claim 79, wherein the electrical signal includes ionic current flow.

81. The system of claim 80, wherein the ionic current flow is blocked upon passage through the nanopore of the single molecule and an electrical signal is generated.

82. The system of claim 56, wherein the optical waveguide is generally structured as an anti-resonant reflecting optical waveguide (ARROW).

83. A system for making parallel optical and electrical measurements, comprising:
    an optical waveguide comprising a generally planar solid-state material and a plurality of parallel channels within the solid-state material, including a Fabry-Perot reflector adjacent to each channel, whereby light injected into the channels is substantially prevented from leaking out of the channels in a transverse direction;
    a port for injecting through each of the channels a sample material;
    a perpendicular waveguide portion for use in injecting light into the channels in a direction which is generally perpendicular to the orientation of the channels;
    means for measuring selected optical and/or electrical properties associated with an analyte in the sample material; and
    an electrical component in fluid communication with the channels to control movement of the analyte in the sample material through the plurality of parallel channels.

84. The system of claim 83, wherein the selected optical properties include transmission, absorption, interference and/or fluorescence characteristics associated with the sample materials over macroscopic distances within the channel.

85. The system of claim 83, wherein the channels may be used to contain the sample material whose light transmission, absorption, and/or interference characteristics are to be measured.

86. The system of claim 85, wherein the means for measuring selected optical and/or electrical properties further comprises a detector of light transmission, absorption, and/or interference characteristics.

87. The system of claim 86 wherein the detector is an optical detector integrated with the optical waveguide on the substrate.

88. The system of claim 87, wherein a single nucleic acid molecule, a single protein molecule, a single amino acid molecule or a single particle from the sample material is detected by the optical detector.

89. The system of claim 86, wherein the detector is a fluorescence detector.

90. The system of claim 86, wherein the detector is a light detector or a Raman scattering detector.

91. The system of claim 83, wherein the sample material is nucleic acid, protein, or amino acid.

92. The system of claim 91, wherein the nucleic acid, protein, or amino acid is separated from a mixture in the sample material.

93. The system of claim 92, wherein a single nucleic acid molecule, a single protein molecule, a single amino acid molecule or a single particle is separated from the mixture.

94. The system of claim 93, wherein a single nucleic acid molecule, a single protein molecule, a single amino acid molecule or a single particle is detected within the optical waveguide.

95. The system of claim 83, wherein the sample material is a single molecule or a single particle.

96. The system of claim 83, wherein the electrical component is an electrophoretic component.

97. The system of claim 96, wherein the electrical component is a first electrode and a second electrode applying a current across a length of the channel.

98. The system of claim 97, further comprising a first reservoir and a second reservoir at opposite ends of the channel and in fluid contact with the channel, the first reservoir in fluid communication with the first electrode and the second reservoir in fluid communication with the second electrode.

99. The system of claim 97, wherein the electrodes are platinum.

100. The system of claim 97, wherein the electrodes are silver/silver chloride.

101. The system of claim 97, wherein the electrodes are microelectrodes integrated on the substrate.

102. The system of claim 83 further comprising a nanopore or micropore, for injecting into the channel an analyte in a sample fluid.

103. The system of claim 102, wherein the nanopore is configured to limit passage of an analyte through the nanopore or micropore to one molecule or one particle at a time.

104. The system of claim 102, wherein an electrical signal is generated upon passage through the nanopore or micropore of the single molecule or single particle.

105. The system of claim 104, wherein the electrical signal includes ionic current flow.

106. The system of claim 83, wherein the electrical properties include ionic current flow.

107. The system of claim 106, wherein the ionic current flow is blocked upon passage through the nanopore or micropore of the single molecule or single particle, and an electrical signal is generated.

108. The system of claim 83, wherein the one or more channels have an index of refraction which is lower than the index of refraction of the surrounding solid-state material.

109. The system of claim 83, wherein the optical waveguide comprises a silicon (Si) substrate and multiple layers of solid state material disposed on the substrate, and a non-solid core extending through at least one of the multiple layers, whereby the non-solid core may be used to contain the sample material.

110. The system of claim 83, wherein the means for measuring selected optical and/or electrical properties associated with the sample material further comprises spatio-temporal synchronization of optical and electrical sensing capability.

111. The system of claim 83, wherein the means for measuring selected optical and/or electrical properties associated with the sample material further comprises simultaneous recording of electrical current blockade signals and optical fluorescence signals or Raman scattering signals with single-molecule sensitivity.

* * * * *

UNITED STATES PATENT AND TRADEMARK OFFICE
CERTIFICATE OF CORRECTION

PATENT NO. : 7,444,053 B2
APPLICATION NO. : 11/376442
DATED : October 28, 2008
INVENTOR(S) : Holger Schmidt et al.

It is certified that error appears in the above-identified patent and that said Letters Patent is hereby corrected as shown below:

Column 33, line 64; Claim 1, line 7, delete "channel" and insert --non-solid core-- therefor.

Signed and Sealed this

Thirtieth Day of November, 2010

David J. Kappos
*Director of the United States Patent and Trademark Office*